United States Patent
Hnojewyj et al.

(10) Patent No.: US 7,351,249 B2
(45) Date of Patent: Apr. 1, 2008

(54) SYSTEMS, METHODS, AND COMPOSITIONS FOR ACHIEVING CLOSURE OF SUTURE SITES

(75) Inventors: Olexander Hnojewyj, Saratoga, CA (US); Bruce Addis, Redwood City, CA (US); Daniel Browne, Palo Alto, CA (US); David Cheung, Santa Cruz, CA (US)

(73) Assignee: NeoMend, Inc., Irvine, CA (US)

( * ) Notice: Subject to any disclaimer, the term of this patent is extended or adjusted under 35 U.S.C. 154(b) by 384 days.

(21) Appl. No.: 10/212,472

(22) Filed: Aug. 5, 2002

(65) Prior Publication Data

US 2003/0040760 A1 Feb. 27, 2003

Related U.S. Application Data

(63) Continuation-in-part of application No. 10/141,510, filed on May 8, 2002, which is a continuation-in-part of application No. 09/780,843, filed on Feb. 9, 2001, now Pat. No. 6,949,114, which is a continuation-in-part of application No. 09/283,535, filed on Apr. 1, 1999, now Pat. No. 6,458,147, which is a continuation-in-part of application No. 09/188,083, filed on Nov. 6, 1998, now Pat. No. 6,371,975.

(51) Int. Cl.
*A61B 17/08* (2006.01)
(52) U.S. Cl. .................................... 606/214
(58) Field of Classification Search ............... 606/148, 606/213, 214, 232; 128/898; 424/443, 448, 424/422–424

See application file for complete search history.

(56) References Cited

U.S. PATENT DOCUMENTS

| | | | |
|---|---|---|---|
| 5,417,699 A | 5/1995 | Klein et al. | |
| 5,527,322 A | 6/1996 | Klein et al. | |
| 5,536,273 A * | 7/1996 | Lehrer | 606/139 |
| 5,536,768 A * | 7/1996 | Kantner et al. | 524/376 |
| 5,583,114 A | 12/1996 | Barrows et al. | |
| 5,626,863 A | 5/1997 | Hubbell et al. | |
| 5,649,959 A * | 7/1997 | Hannam et al. | 606/213 |
| 5,725,551 A * | 3/1998 | Myers et al. | 606/213 |
| 5,733,563 A | 3/1998 | Fortier | |
| 5,746,755 A * | 5/1998 | Wood et al. | 606/148 |
| 5,752,964 A * | 5/1998 | Mericle | 606/148 |
| 5,842,519 A * | 12/1998 | Sydansk | 166/295 |
| 5,844,016 A | 12/1998 | Sawhney et al. | |
| 5,861,004 A * | 1/1999 | Kensey et al. | 606/213 |
| 5,874,500 A | 2/1999 | Rhee et al. | |
| 5,936,035 A | 8/1999 | Rhee et al. | |
| 5,986,043 A | 11/1999 | Hubbell et al. | |
| 6,166,130 A | 12/2000 | Rhee et al. | |
| 6,177,095 B1 | 1/2001 | Sawhney et al. | |

(Continued)

FOREIGN PATENT DOCUMENTS

WO WO 01/66017 9/2001

*Primary Examiner*—Michael J. Hayes
*Assistant Examiner*—Victor Nguyen
(74) *Attorney, Agent, or Firm*—Ryan, Krumholz & Manion, S.C.

(57) ABSTRACT

Systems and methods employ functional instruments to close incisions and wounds using a suture knot in combination with a biocompatible material composition. The systems and methods are well suited for use, for example, at a vascular puncture site following a vascular access procedure.

10 Claims, 25 Drawing Sheets

U.S. PATENT DOCUMENTS

| | | |
|---|---|---|
| 6,371,975 B2 | 4/2002 | Cruise et al. |
| 6,458,147 B1 | 10/2002 | Cruise et al. |
| 6,514,534 B1 | 2/2003 | Sawhney |
| RE38,158 E | 6/2003 | Barrows et al. |
| 6,830,756 B2 | 12/2004 | Hnojewyj |
| 6,887,974 B2 | 5/2005 | Pathak |
| 6,899,889 B1 | 5/2005 | Hnojewyj et al. |
| RE38,827 E | 10/2005 | Barrows et al. |
| 7,057,019 B2 | 6/2006 | Pathak |
| 2001/0031948 A1 | 10/2001 | Cruise et al. |
| 2001/0047187 A1 | 11/2001 | Milo et al. |
| 2001/0051813 A1 | 12/2001 | Hnojewyj |
| 2003/0100921 A1 | 5/2003 | Addis et al. |

* cited by examiner

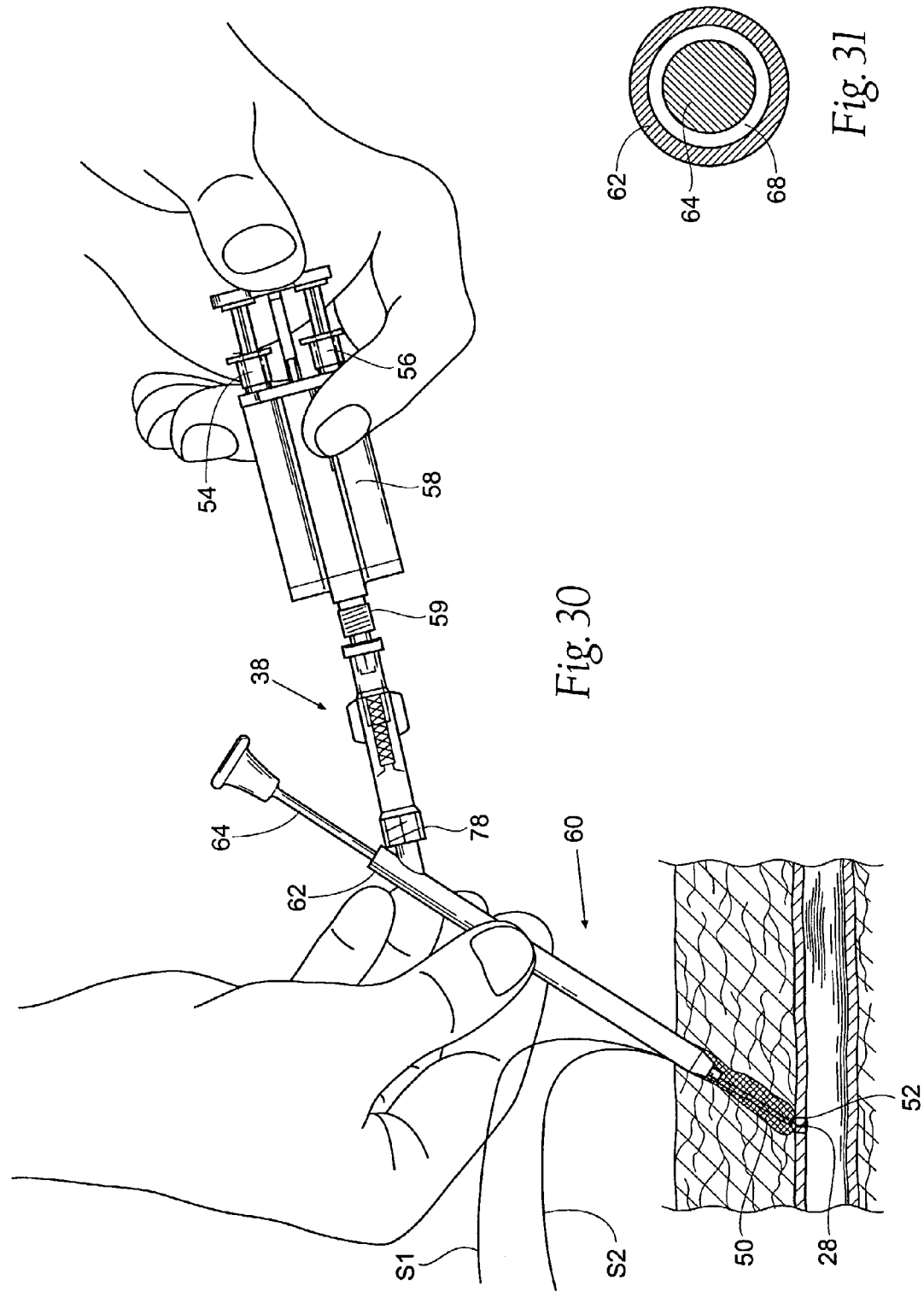

SYSTEMS, METHODS, AND COMPOSITIONS FOR ACHIEVING CLOSURE OF SUTURE SITES

RELATED APPLICATIONS

This application is a continuation-in-part of U.S. patent application Ser. No. 10/141,510, filed May 8, 2002 and entitled "Systems, Methods, and Compositions for Achieving Closure of Vascular Puncture Sites," which is a continuation-in-part of U.S. patent application Ser. No. 09/780,843, filed Feb. 9, 2001, and entitled "Systems, Methods, and Compositions for Achieving Closure of Vascular Puncture Sites" (now U.S. Pat. No. 6,949,114), which is a continuation-in-part of U.S. patent application Ser. No. 09/283,535, filed Apr. 1, 1999, and entitled "Compositions, Systems, And Methods For Arresting or Controlling Bleeding or Fluid Leakage in Body Tissue" (now U.S. Pat. No. 6,458,147), which is itself a continuation-in-part of U.S. patent application Ser. No. 09/188,083, filed Nov. 6, 1998 and entitled "Compositions, Systems, and Methods for Creating in Situ, Chemically Cross-linked, Mechanical Barriers" (now U.S. Pat. No. 6,371,975), all of which are incorporated herein by reference.

FIELD OF THE INVENTION

The invention generally relates to the systems and methods for closing suture sites in body tissue to affect desired therapeutic results.

BACKGROUND OF THE INVENTION

There are many therapeutic indications today that pose problems in terms of technique, cost efficiency, or efficacy, or combinations thereof.

For example, following an interventional procedure, such as angioplasty or stent placement, a 5 Fr to 9 Fr arteriotomy remains. Typically, the bleeding from the arteriotomy is controlled through pressure applied by hand, by sandbag, or by C-clamp for at least 30 minutes. While pressure will ultimately achieve hemostasis, the excessive use and cost of health care personnel is incongruent with managed care goals.

Various alternative methods for sealing a vascular puncture site have been tried. For example, devices that surgically suture the puncture site percutaneously have been used. Suture is used because it is perceived as providing a reliable and tight closure of any wound where the suture can be properly placed, tied, and tightened. Suturing is relatively straightforward in most open surgical procedures. However, placement and tying of sutures in closed, minimally invasive procedures, e.g., in laparoscopic or catheter-based procedures, often require placement, tying, and tightening of a suture knot transcutaneously through a tissue tract. A variety of devices have been developed for the transcutaneous placement, tying, and tightening of suture knots through a tissue tract.

For example, when used for closure of vascular punctures, these devices deploy within a tissue tract to place a suture loop through tissue on opposite sides of the vascular puncture. Two free ends of the suture loop are brought out through the tissue tract. The loops are externally tied by the attending physician, forming a sliding knot in the suture loop. A tool, called a "knot pusher," is deployed through the tissue tract for cinching the slidable knot over the loop. When used to suture vessel punctures, the knot pusher advances the knot through the tissue tract to locate the knot over the adventitial wall of the blood vessel, resulting in puncture edge apposition.

Despite the skill and due care involved in placing, tying, and tightening a suture knot using these devices, seepage of blood and fluids at the suture site and into the tissue tract can still occur. Under these circumstances, a "dry" femoral closure cannot be achieved. Hematoma formation can result, which can prolong a patient's return to ambulatory status without pain and immobilization.

Thus, there remains a need for fast and straightforward systems and methods to achieve suture closure through a tissue tract, which are substantially free of blood or fluid leakage about the suture site and into the tissue tract.

SUMMARY OF THE INVENTION

One aspect of the invention provides systems and methods for sealing a suture knot. The systems and methods form a suture knot and discharge a liquid closure material adjacent the suture knot. The liquid closure material reacts after discharge to form a solid closure adjacent the suture knot. In one embodiment, a knot pusher is used to form the suture knot, and the liquid closure material is discharged through the knot pusher.

The systems and methods can be used for sealing a puncture site in a blood vessel.

Another aspect of the invention provides a knot pusher comprising a body including a passage having a distal end. The body is sized and configured to engage a suture knot adjacent the distal end of the passage. A fitting is carried by body. The fitting is sized and configured for introducing a liquid closure material into the passage for discharge through the distal end adjacent the suture knot. The liquid closure material reacts after discharge to form a solid closure adjacent the suture knot.

In one embodiment, the body of the knot pusher is sized and configured for locating the suture knot in a tissue puncture tract.

In one embodiment, the body of the knot pusher is sized and configured for locating the suture knot adjacent a puncture site in a blood vessel.

Another aspect of the invention provides an assembly for sealing a puncture site in a blood vessel. The assembly comprises a suture knot formed at the puncture site, and a dispenser to discharge a liquid closure material adjacent the suture knot. The liquid closure material reacts after discharge to form a solid closure adjacent the suture knot.

In one embodiment, the liquid closure material comprises a first component including an electrophilic polymer material having a functionality of at least three; a second component including a nucleophilic material that, when mixed with the first component and after discharge as a liquid, cross-links with the first component to form the solid closure, a non-liquid, three-dimensional barrier; and a buffer material mixed with the second component. The first component can include a multi-armed polymer structure, such as, e.g., poly(ethylene glycol), poly(ethylene oxide), poly (vinyl alcohol), poly(vinylpyrrolidinone), poly(ethyloxazoline), and poly(ethylene glycol)-co-poly(propylene glycol) block copolymers. The second component can include hydrophilic protein, such as, e.g., serum, serum fractions, solutions of albumin, gelatin, antibodies, fibrinogen, serum proteins, and recombinant or natural human serum albumin. The buffer material can include, e.g., tris-hydroxymethylaminomethane and/or sodium carbonate anhydrous.

DESCRIPTION OF THE DRAWINGS

FIGS. 5 to 11 illustrate the use of the formative component assembly, that forms a part of the system shown in FIG. 1, to deliver a closure composition to the knot pusher shown in FIGS. 2 and 3, wherein FIGS. 5 and 6 are perspective views illustrating the insertion of the vial component of the formative component assembly; FIG. 7 is a perspective view illustrating the insertion of the syringe component of the formative component assembly; FIG. 8 is a side section view illustrating the coupling the assembled formative component assembly to the mixer element, which, in turn, is coupled to the knot pusher shown in FIGS. 2 and 3; FIG. 9 is a side section view illustrating the advancement of the syringe plunger component of the formative component assembly and further illustrating the transfer of the liquid component in the syringe into the vial containing the solid component mixture of the liquid and the reconstituted solid components in the vial; FIG. 10 is a side section view illustrating the urging of the mixture from the vial through the second needle component of the formative component assembly and into the mixer element; and FIG. 11 is a side section view illustrating the syringe and vial after the mixture has been transferred from the vial to the mixer element.

FIGS. 29 and 30 are diagrammatic views of the blood vessel puncture site shown in FIG. 28, as a closure composition is being delivered through the knot pusher to envelope the suture closure and fill the tissue tract.

FIG. 31 is a section view of the knot pusher shown in FIG. 26, taken generally along line 31-31 in FIG. 26 with the knot pushing element coaxially advanced through the outer sheath and forming between them a passage through which the closure composition is delivered to envelope the suture closure and fill the tissue tract, as FIGS. 29 and 30 show.

DETAILED DESCRIPTION

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

The systems and methods disclosed herein are shown in the particular context of closing a vascular puncture site. That is because the systems and methods are well suited for use in this indication, and this indication thus provides a representative embodiment for purposes of description. Still, it should be appreciated that the systems and methods described can, with appropriate modification (if necessary), be used for diverse other indications as well, and in conjunction with delivery mechanisms that are not necessarily catheter-based. For example, the systems and methods can be used with delivery mechanisms which use cannulas, e.g., for the purpose of filling tissue voids or aneurysms, or for tissue augmentation. As yet another example, the systems and methods can be used to deliver drug or cells to targeted locations.

I. System Overview

Figure 1:
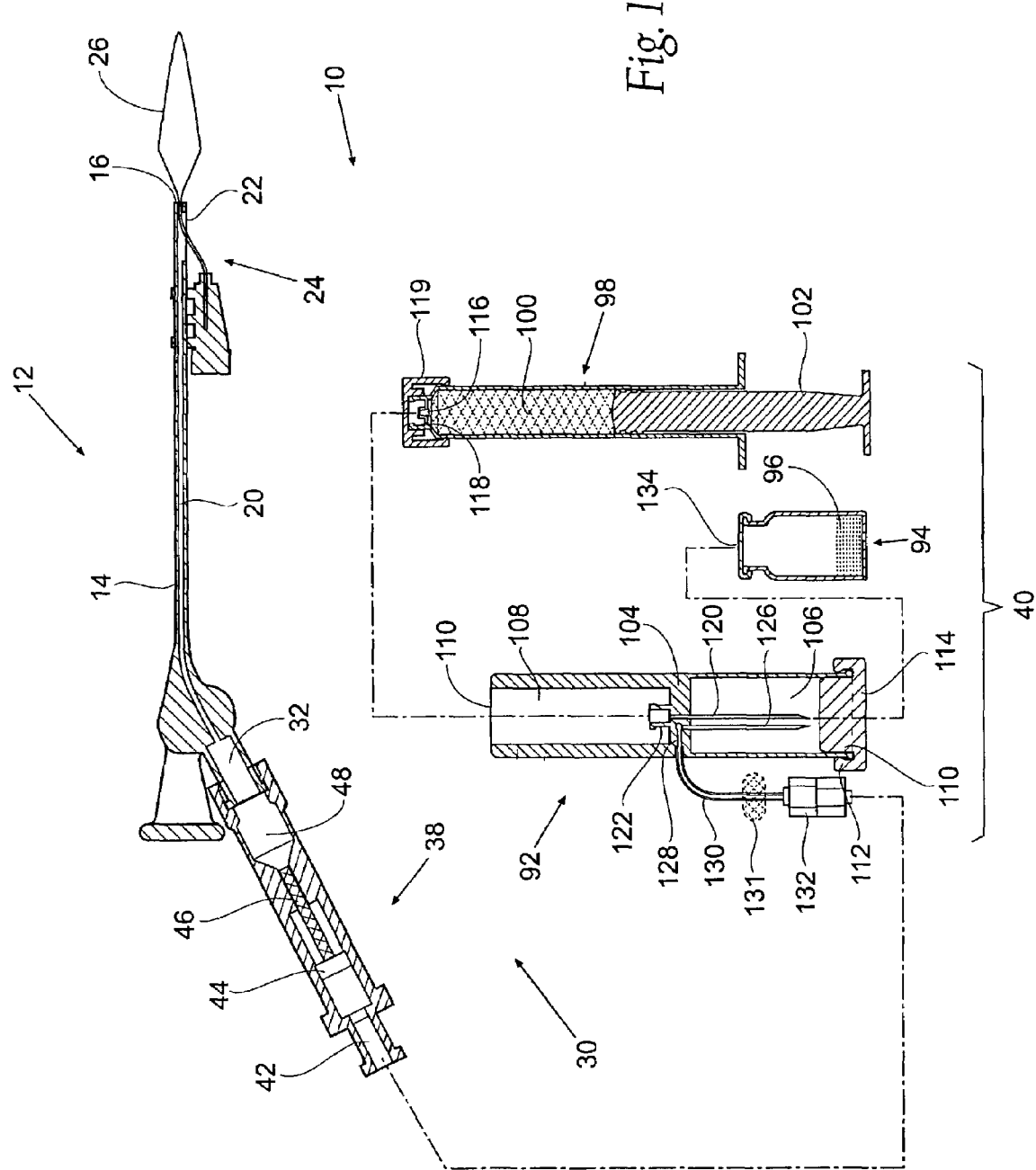
FIG. 1 is a plane view of a system of functional instruments, with portions broken away and in section, for the closure of incisions and wounds using a suture knot in combination with a biocompatible material composition, the system including a knot pusher and a component introducer/mixer assembly.

FIG. 1 shows a system 10 of functional instruments for the closure of incisions and wounds using a suture knot in combination with a biocompatible material composition. The system 10 is well suited for use, for example, at a vascular puncture site following a vascular access procedure.

As arranged in FIG. 1, the system 10 includes a knot pusher 12 and a component introducer/mixer assembly 30.

In use (as will be described in greater detail later), the knot pusher 12 is sized and configured to be manually deployed during the course of a surgical procedure where a suture loop has been formed in tissue, to close an incision or wound, or for any other purpose. In such procedures, a slidable knot is formed in the suture loop, and the knot pusher 12 is used to engage and advance the knot to close the loop.

Also in use (as will be described in greater detail later), the component introducer/mixer assembly 30 is sized and configured during the course of such surgical procedures, to be coupled to the knot pusher 12 to introduce a biocompatible material composition through the knot pusher 12 into contact with the suture knot in situ. The biocompatible material composition produces a solid, three dimensional matrix about the suture knot. The matrix prevents seepage or leakage of blood and fluids in the area of the suture knot.

The system 10 thereby makes possible, through a combination of suturing, augmented by the deposit of a biocompatible matrix material, a dry suture closure, which is substantially free of blood or fluid leakage.

A. The Knot Pusher

Figure 2:
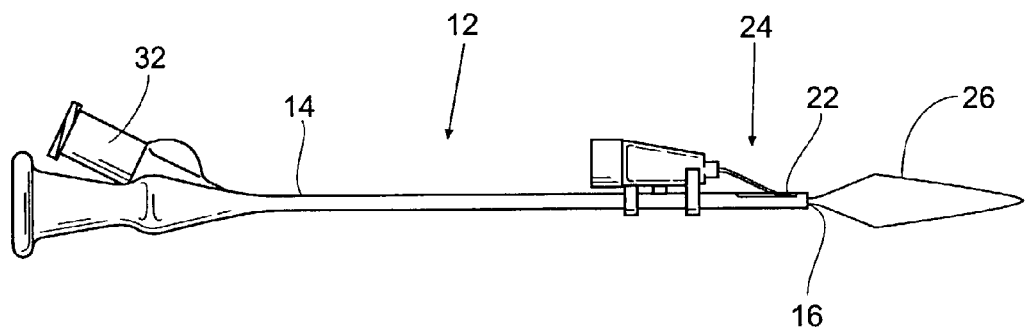
FIG. 2 is a side view of the knot pusher that forms a part of the system shown in FIG. 1.
Figure 3:
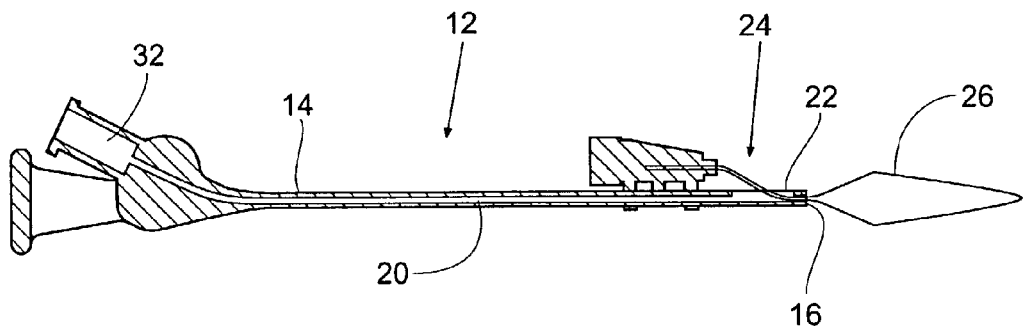
FIG. 3 is a side section view of the knot pusher that forms a part of the system shown in FIG. 1.
Figure 16:
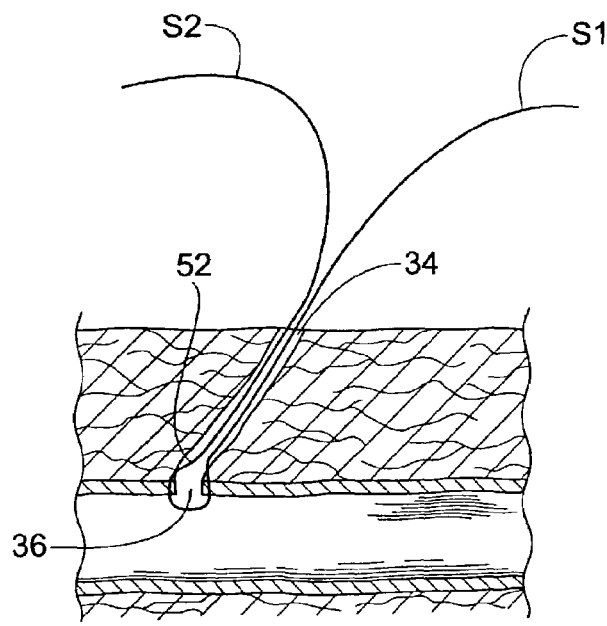
FIG. 16 is a diagrammatic view of blood vessel puncture site formed to enable the delivery of a diagnostic or therapeutic instrument through a vascular sheath, after removal of the diagnostic or thereapeutic instrument and the placement of a suture loop through the puncture site.

As shown in FIGS. 1 to 3, the knot pusher comprises an elongated body or shaft 14. In the illustrated embodiment, the shaft 14 is sized and configured for passage through a transcutaneous tissue tract to a vessel puncture site. As shown in FIG. 16, the tissue track 34 typically will have been previously formed by a vascular introducer or cannula, through which a desired therapeutic or diagnostic instrument is first introduced through a puncture site 36 into the vessel, e.g., to perform coronary angioplasty. After performing the intended procedure, the therapeutic or diagnostic instrument and introducer are withdrawn, leaving the puncture site 36 and the tissue track 34.

For use in this indication, the shaft 14 will typically have a length in the range from about 7 cm to 10 cm. Furthermore, for use in this indication, the outside diameter of the shaft 14 is desirably sized to seal the tissue track 34 through which it is introduced (see FIG. 21), so that its presence is hemostatic. In this context, the outside diameter of the shaft 14 is desirably selected to match the outside diameter of the vascular introducer, e.g., from 6 Fr. to 10 Fr, so that the shaft 14, when deployed, will block substantial flow of blood and fluid from the puncture site 36 up the tissue track 34 (as shown in FIGS. 20 and 21).

As shown in FIG. 3, an interior passage 20 extends through the shaft 14. One end of the passage 20 exits the distal end 16 of the shaft 14. A side wall slot 22 formed on the distal end 16 opens into the passage 20.

In this arrangement, the knot pusher 12 includes a suture threading fixture 24. The fixture 24 is releasably carried by the distal end 16 of the shaft 14 in alignment with with the slot 22. The fixture 24 includes a threader 26. The threader 26 desirably comprises a loop of thin, flexible wire that is initially positioned so as to pass through the slot 22, into the passage 20, and out the distal end 16 of the shaft 14.

Figure 17:
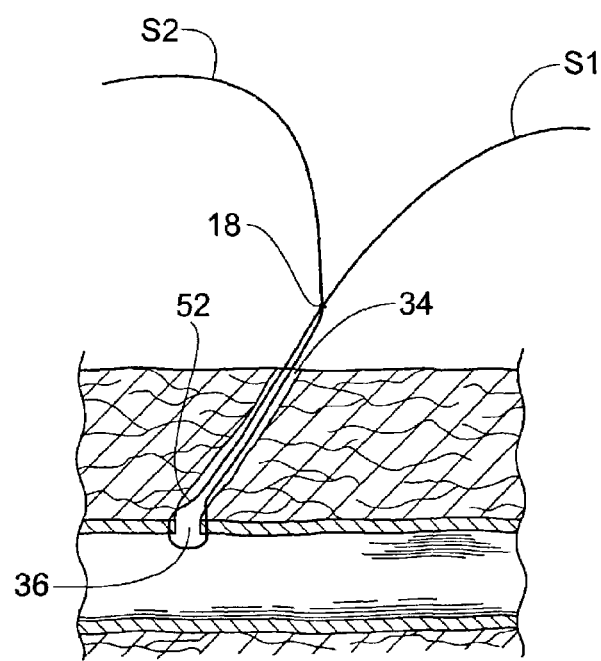
FIG. 17 is a diagrammatic view of the blood vessel puncture site shown in FIG. 16, after formation of a slidable knot in the suture loop.
Figure 19:
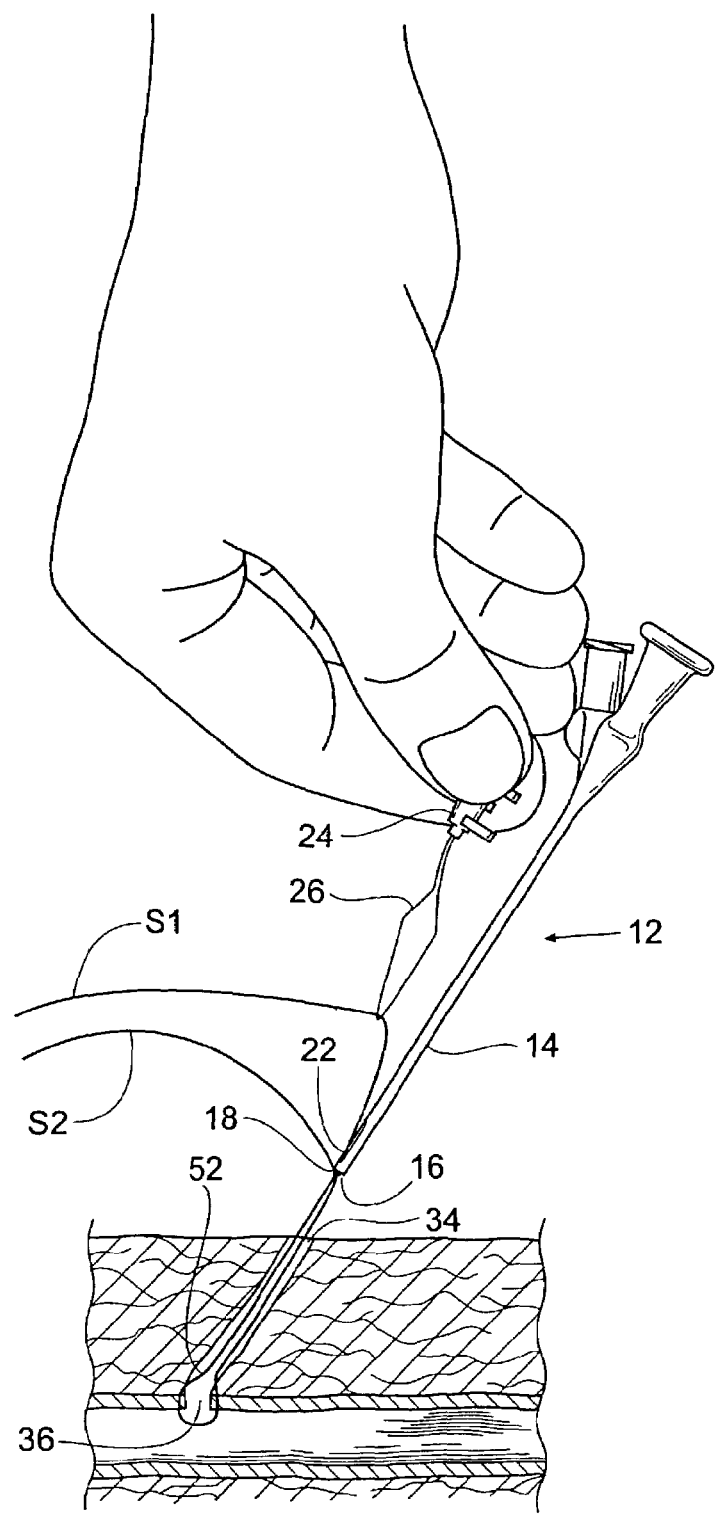
FIG. 19 is a diagrammatic view of the blood vessel puncture site shown in FIG. 18, after threading of suture in the knot pusher and as the knot pusher is advanced toward the tissue tract, pushing the slidable knot.
Figure 20:
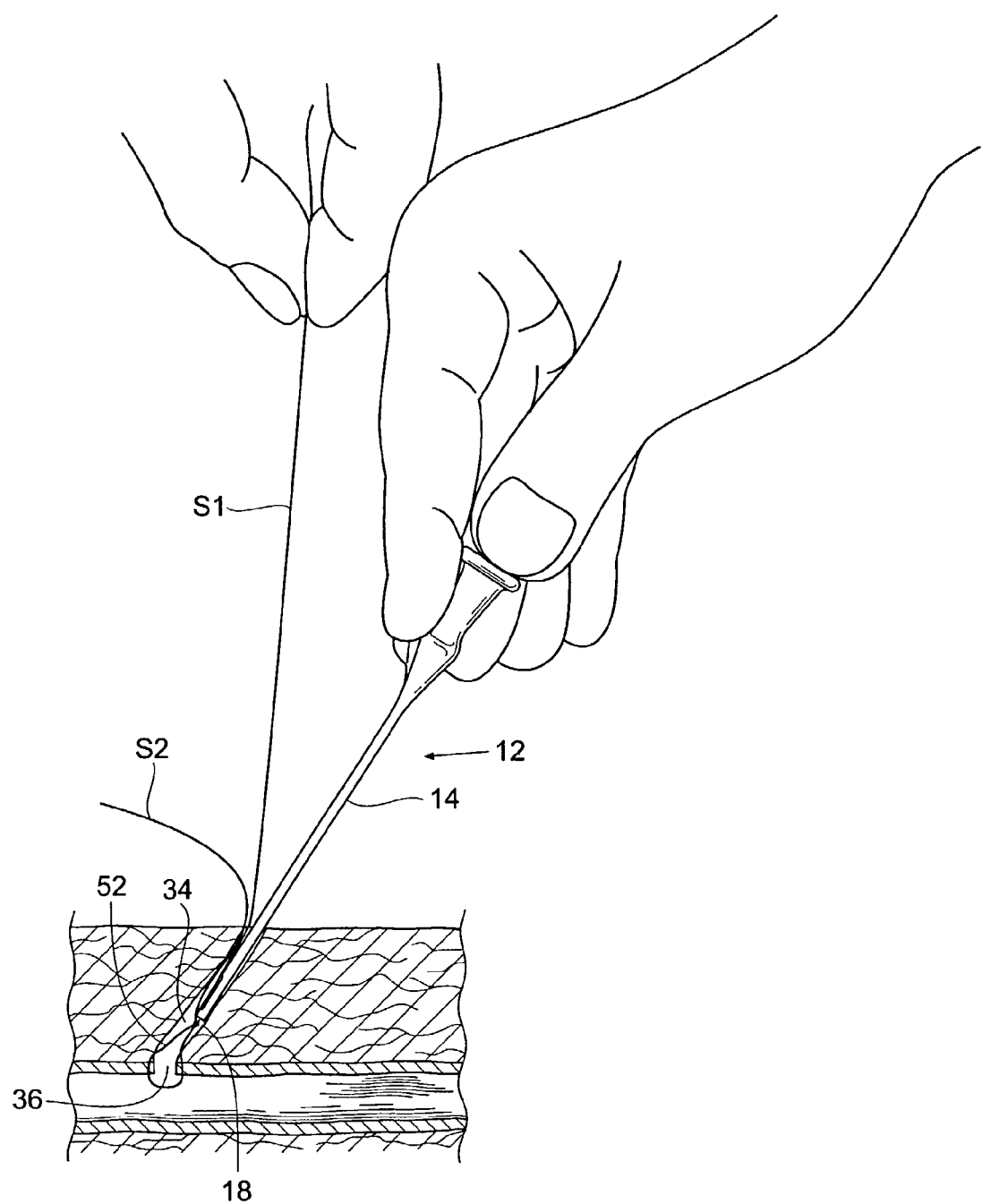
FIGS. 20 and 21 are diagrammatic views of the blood vessel puncture site shown in FIG. 19, as the knot pusher is advanced through the tissue tract to form a suture closure at the vessel puncture site.
Figure 21:
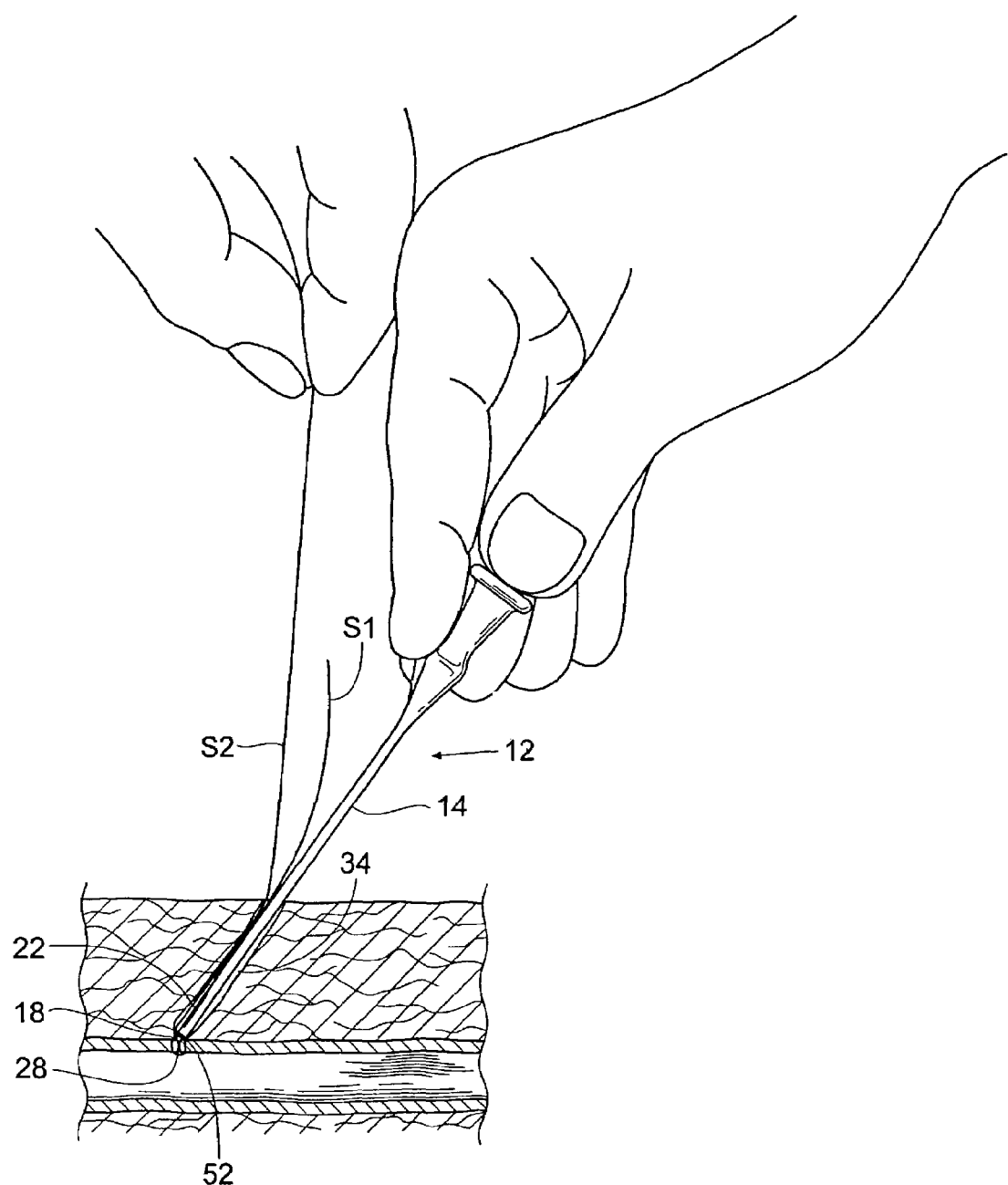

The fixture 24 (see FIGS. 18 and 19) is configured to thread suture S1 through the passage 20 and slot 22 and thereby engage and advance a slidable knot 18 in the tissue tract 34 (see FIG. 20). The slidable knot 18 will have been previously formed (see FIGS. 16 and 17) in a suture loop 20 placed at the puncture site 36, e.g., using a device described in U.S. Pat. No. 5,417,699 or U.S. Pat. No. 5,527,322, which are both incorporated herein by reference. As FIGS. 16 and 17 show, the slidable knot 18 is formed after formation of the suture loop 52 by tying the two free ends S1 and S2 of suture forming the loop 52.

Figure 18:
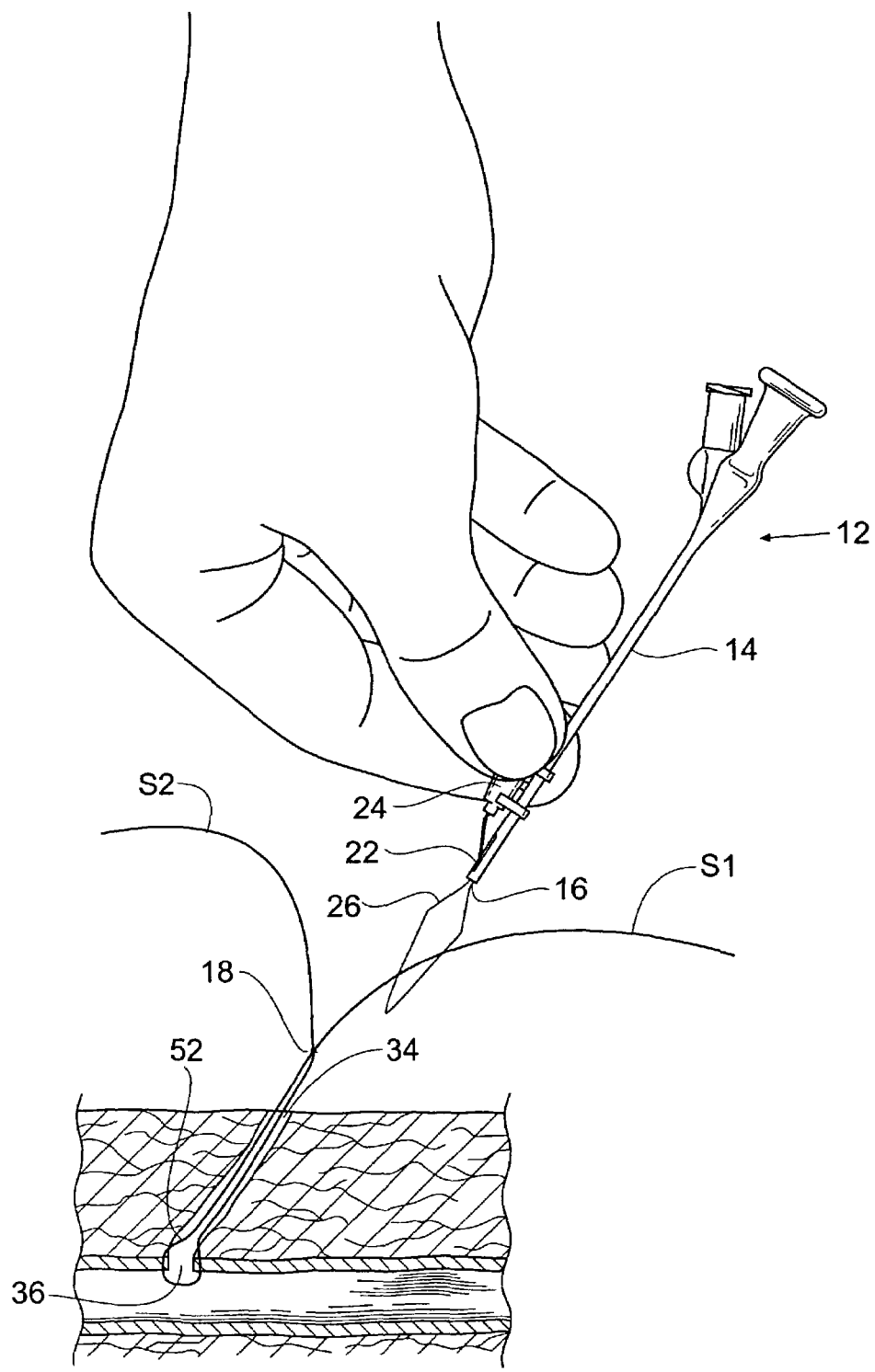
FIG. 18 is a diagrammatic view of the blood vessel puncture site shown in FIG. 17, showing the threading of suture in the knot pusher after formation of the slidable knot.

More particularly, after the slidable knot 18 is formed, the threading fixture 24 threads a free end S1 through the passage 20 and slot 22 of the knot pusher 12. Using the treading fixture 24, the attending physician captures a free end S1 of the suture within the loop of the threader 26 (FIG. 18). The physician disconnects the fixture 24 from the shaft 14, and pulls the fixture 24 distally to draw the threader 26 and, with it, the free end S1 of the suture through the distal shaft end 16 into the passage 20, and then through the slot 22 (FIG. 19). Upon releasing the free end S4 of the suture from the threader 26, and discarding the fixture 24, the physician can then urge the knot pusher 12 through the tissue tract 34, while holding the free suture end S1, to advance and tighten the slidable knot 18 within the tissue tract 34, as FIGS. 20 and 21 show. The knot pusher 12 engages and advances the slidable knot 18 over the free end S1 of the suture, to close the loop 20 and bring the edges of the puncture site 36 into apposition. The slidable knot 18 can then be tightened by pulling on the other free end S2 of the suture, forming a suture closure 28 (shown in FIG. 21).

B. The Component Introducer/Mixer Assembly

Figure 22:
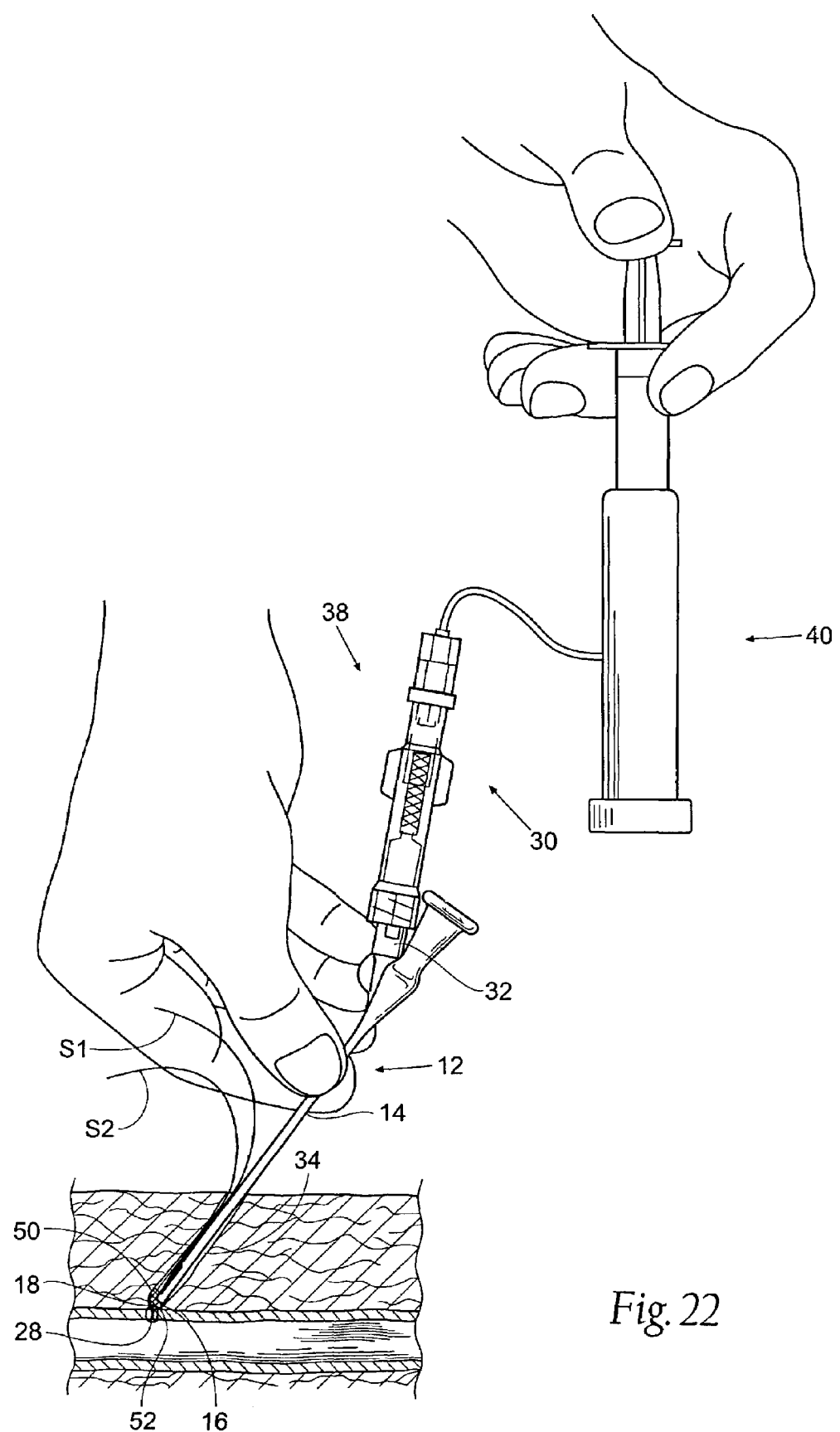
FIGS. 22 and 23 are diagrammatic views of the blood vessel puncture site shown in FIGS. 20 and 21, as a closure composition is being delivered through the knot pusher to envelope the suture closure and fill the tissue tract.
Figure 23:
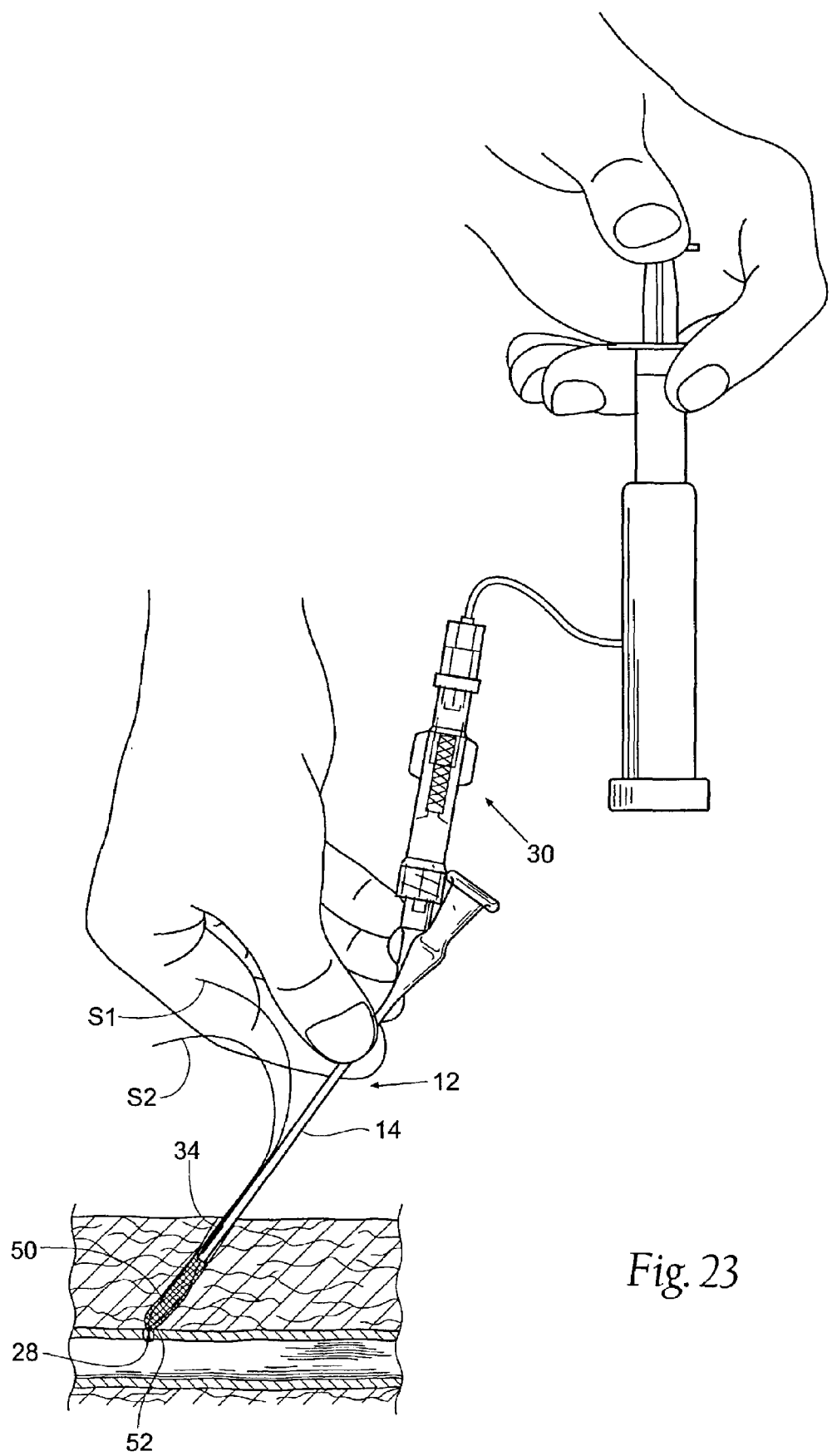
Figure 24:
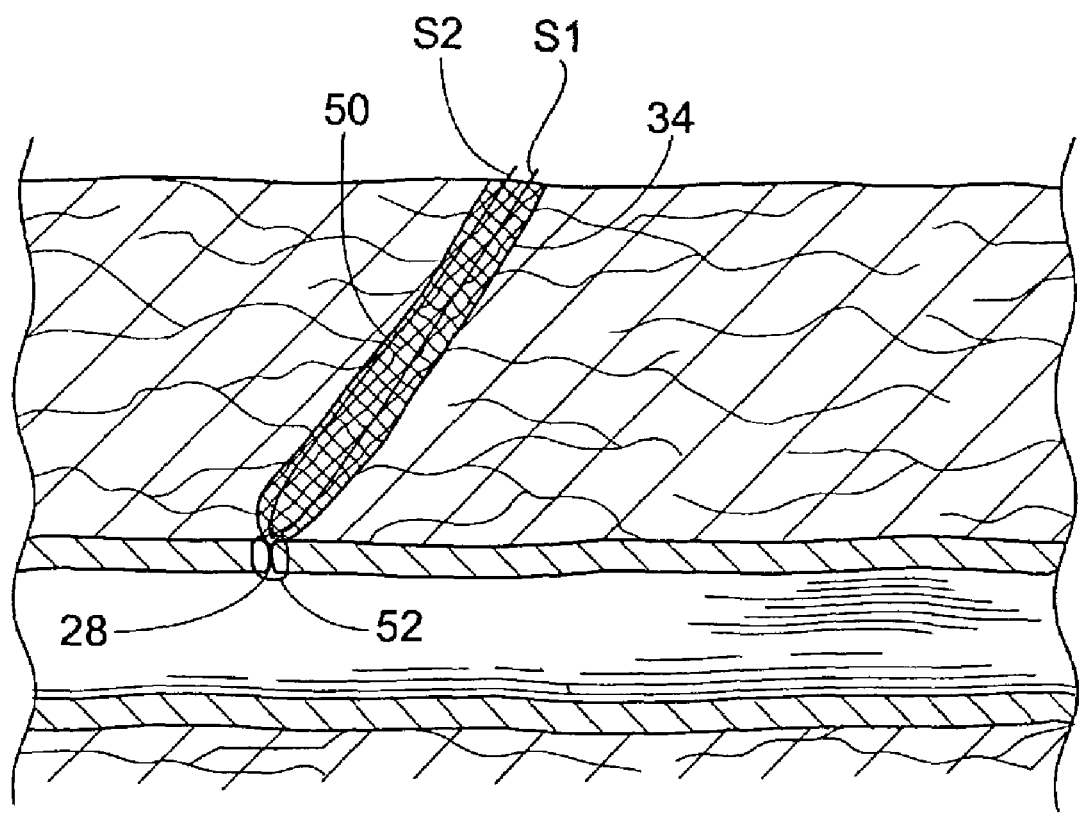
FIG. 24 is a diagrammatic view of the blood vessel puncture site shown in FIGS. 222 and 23, after removal of knot pusher and after the closure composition has formed a barrier to seal the suture closure and tissue tract.

Upon forming the suture closure 28 using the knot pusher 12 in the manner just described, the component introducer/mixer assembly 30 is assembled and coupled to the knot pusher 12 (see FIG. 22). In use (see FIGS. 22 and 23), the assembly 30 places a biocompatible material composition 50 about the suture closure 28 outside the blood vessel and, desirably, at least partially up the tissue tract 34 from the puncture site 36. Most desirably, at the end of the procedure, the composition 50 fills the tissue tract 34, as FIG. 24 shows. The biocompatible material composition 50 desirably produces a solid, three dimensional matrix that prevents seepage of blood and fluids through the suture closure 28 and up the tissue tract 34. The system 10 thereby creates a dry closure, which is substantially free of blood or fluid leakage about the suture closure 28 and in the tissue tract 34.

The biocompatible material composition 50 can take various forms. Desirably, the biocompatible material composition 50 is comprised of two or more formative components which are mixed by the assembly 30 and introduced in a liquid state through the knot pusher 12 transcutaneously to the suture closure 28. Upon mixing, the formative components react, in a process called "gelation," to transform in situ from the liquid state, to a semi-solid (gel) state, and then to the biocompatible solid state.

In the solid state, the composition 50 takes the form of a non-liquid, three-dimensional network. Desirably, the solid material composition 50 exhibits strength (adhering it to adjacent tissue), cohesive strength (forming a mechanical barrier that is resistant to blood pressure and blood seepage), and elasticity (accommodating the normal stresses and strains of everyday activity). These properties alone can provide an effective closure to the vascular puncture site, without use of a suture closure 28. However, when used with a suture closure 28, the properties of the composition 50 serve to significantly enhance and augment the localized closure properties of the suture itself.

The solid material composition 50 is also capable of transforming over time by physiological mechanisms from the solid state to a biocompatible liquid state, which can be cleared by the body, in a process called "degradation."

The components forming the material composition 50 can vary. Generally speaking, however, the components will include a solid component and a liquid component, which serves as a diluent for the solid component. Mixing of these two components initiates a chemical reaction, by which the liquid mixture transforms into a solid composition.

A port 32 on the knot pusher 12 (see FIGS. 1 to 3) communicates with proximal end of the passage 20. The port 32 permits coupling of the component introducer/mixer assembly 30 to the knot pusher 12 (see FIG. 22).

The assembly 30 itself can be variously constructed. In the embodiment shown in FIG. 1, the introducer/mixer assembly 30 includes a mixing assembly 38 and a formative component assembly 40. It is the purpose of the mixing assembly 38 and the formative component assembly 40 to facilitate the mixing of components for delivery through the knot pusher 12 to the suture closure 28.

(i) The Mixing Element

Figure 4:
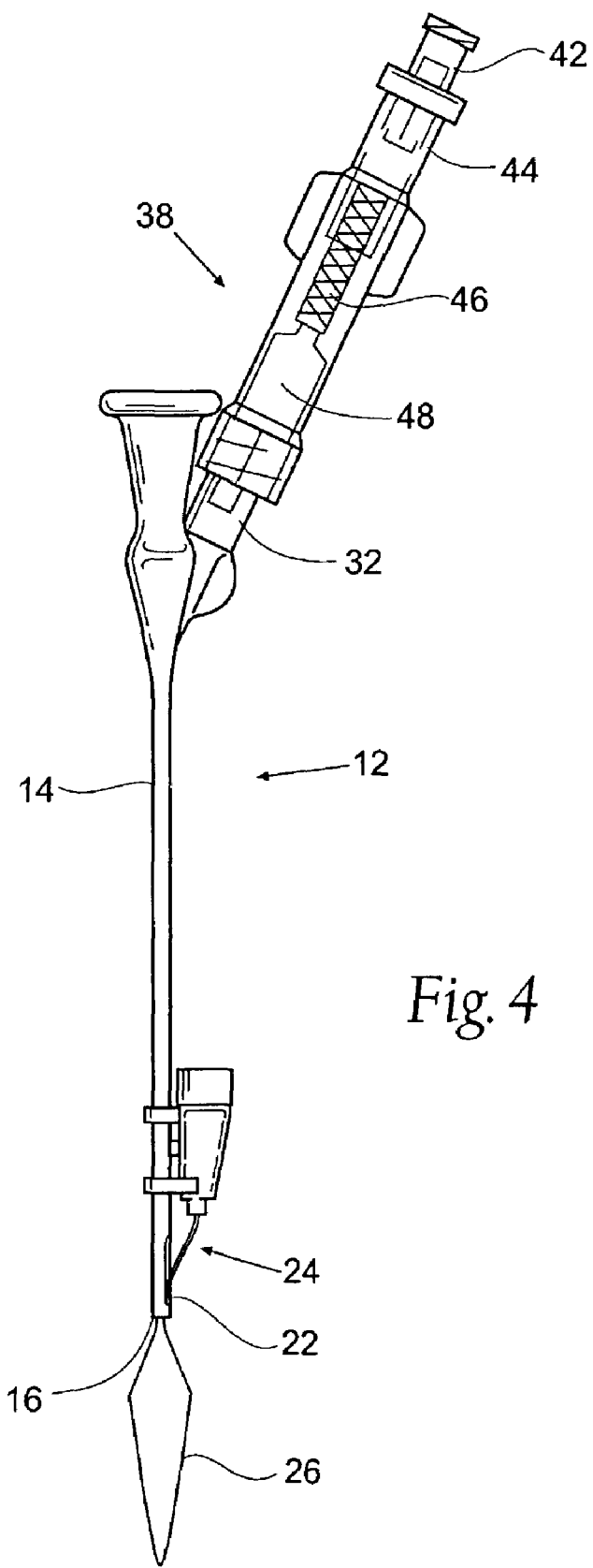
FIG. 4 is a side view of a mixing element, which forms a part of the system shown in FIG. 1, coupled for use to the knot pusher shown in FIGS. 2 and 3.

The mixing assembly 38 (see FIGS. 1 and 4) couples at one end to the port 32 of the knot pusher 12, to thereby establish communication with the interior passage 20. The other end of the mixing assembly 38 includes a luer fitting 42 that, in use, couples to the formative component assembly 40 (see FIG. 8), to thereby establish communication between the assembly 40 and the interior passage 20 through the mixing assembly 38.

In the illustrated embodiment (as best shown in FIG. 1), the mixing assembly 38 includes, in the direction of flow from the formative component assembly 40 toward the passage 20, an in-line syringe activated check valve 44, an in-line mixer 46, and an in-line air accumulator 48.

The in-line syringe activated check valve 44 can take various forms. In the illustrated embodiment, the valve 44 takes the form of a conventional, needleless slip luer lock valve made by Qosina (Edgewood, N.Y.), Product Number 80360. The valve 44 is normally closed to prevent back flow of blood or other liquid material through the assembly 38. Back flow of blood, in particular, from the passage 20 toward the formative component assembly 40 is undesirable, because it creates the potential for blood contact and deposits material that can interfere or compete with the desired reaction between the liquid components that form the material composition. Connection of a conventional luer fitting carried by the formative component assembly 38 (for example, fitting 132 shown in FIGS. 1 and 9) opens the valve 44 to allow the introduction of the liquid components that form the material composition.

The components of the material composition come into intimate mixing contact in the liquid state in the inline mixer 46. In this way, effective mixing can be achieved outside the knot pusher 12. Thus, mixing is not entirely dependent upon the dimensions or lengths of the flow paths within the knot pusher 12. The mixer 46 comprises a mixing structure, which can vary. For example, the mixer 46 can comprise a spiral mixer manufactured by TAH Industries, Inc. (Robbinsville, N.J.), Part Number 121-090-08.

The in-line air accumulator 48 comprises a chamber that has an interior volume sized to trap air that can reside in the material composition applicator at time of use.

(ii) The Formative Component Assembly

In the illustrated embodiment (see FIGS. 1 and 8), the formative component assembly 40 comprises a unitary applicator 92 in which a vial 94 holding a solid component 96 and a syringe 98 holding a liquid component 100 can be placed and kept separate in interior compartments.

Axial advancement of the syringe plunger 102 (see FIG. 9) propels the liquid 100 into the vial 94 and brings the two components 96 and 100 together within the vial 94 by placing the solid component 96 into suspension within the liquid component 100. The force created by this process also urges the liquid suspension into the mixing assembly 38 for further mixing and delivery through the knot pusher passage 20.

The applicator 92 includes a partition 104 (see FIG. 1) that divides the applicator 92 into a first compartment 106 and a second compartment 108, each having an open end 110. The first compartment 106 is sized and configured to receive and hold the vial 94. The first compartment 106 includes a flanged end region 112 that serves to support the applicator 92 in an upright position (e.g., standing on a table). The flanged region 112 further serves to receive a cap 114, as will be described in greater detail later. The second compartment 108 is sized and configured to receive and hold the syringe 98. The applicator 92 can be made of any suitable inert, rigid plastic or metal material. In a representative embodiment, the first compartment 106 is, e.g., 2½ inches long, the second compartment 108 is 2 inches long, and the applicator 92 is 1 inch high. This arrangement readily accommodates a conventional vial 94 and a conventional syringe 98.

The syringe 98 can be a conventional syringe 98 having a plunger 102. The dispensing end 116 includes a luer fitting 118. The syringe 98 is aseptically pre-filled with the liquid component 100 and a cap 119 is placed over the dispensing end 116 to prevent leakage and evaporation of the contents.

Figure 7:
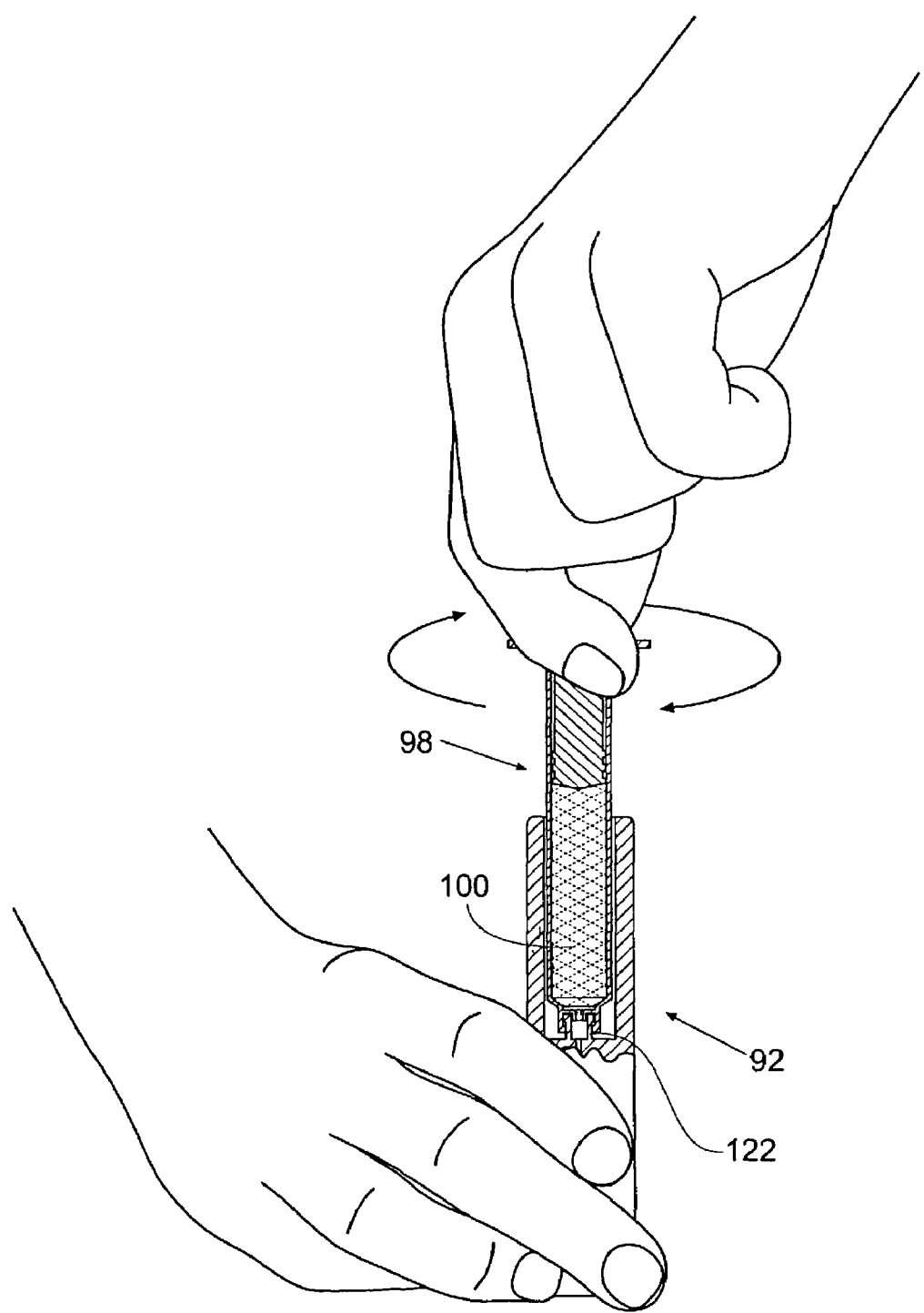

As FIG. 1 shows, a first needle 120 extends along the central line axis of the applicator 92 and couples the syringe 98 to the vial 94 via a luer fitting 122 that mates with the luer fitting 118 on the syringe 98 (also see FIG. 7). The needle 120 thereby provides communication between the first and second compartments 106 and 108. Desirably, the needle 120 includes a plurality of side holes that serve to uniformly introduce the contents of the syringe 98 into the vial 94 (see FIG. 9).

As FIG. 1 shows, a second needle 126 is offset from the central line axis of the applicator 92 and serves to couple the vial 94 to a molded passage 128 that traverses the wall of the second compartment 108. The molded passage 128 is coupled to the proximal end of a length of flexible tubing 130. The distal end of the tubing 130 includes a luer fitting 132 adapted to couple to the luer fitting 42 on the mixing assembly 38, as already described. His arrangement provides fluid communication between the vial 94 and the mixing assembly 38. Optionally, an in-line air vent 131 (shown in phantom lines in FIG. 1), made, e.g., from a sintered plastic material, can be located in the tubing 130, or otherwise placed in communication with the tubing 130, to allow residual air to vent from fluid prior to entering the mixing assembly 38.

The vial 94 is a conventional pharmaceutical vial 94 sized to hold the solid component 96 and a pre-defined volume of the liquid component 100, i.e., the volume of liquid component 100 pre-filled in the syringe 98. The vial 94 includes a septum 134 configured to be pierced and penetrated by the needles 120 and 126 when the vial 94 is properly positioned within the first compartment 106.

To aid in positioning and securing of the vial 94 within the compartment 106, the applicator 92 includes a selectively removable cap 114, as previously noted. The cap 114 mates with the applicator 92, e.g., by snap-fit engagement with the flanged region 112 on the applicator 92. Desirably (see FIG. 6), the cap 114 extends into the first compartment 106 to position and hold the vial 94 in a desired position after the septum 134 has been pierced by the needles 120 and 126.

Figure 5:
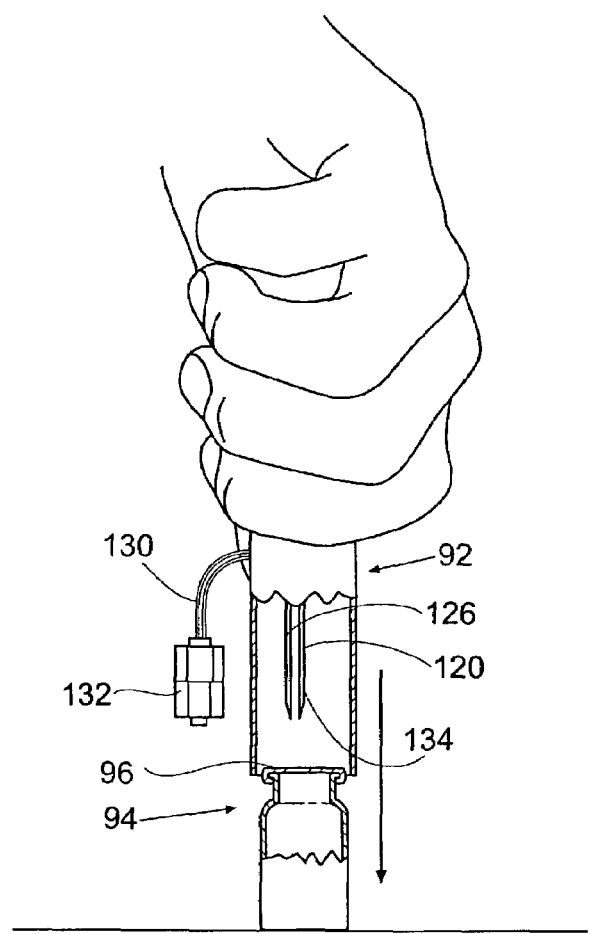
Figure 6:
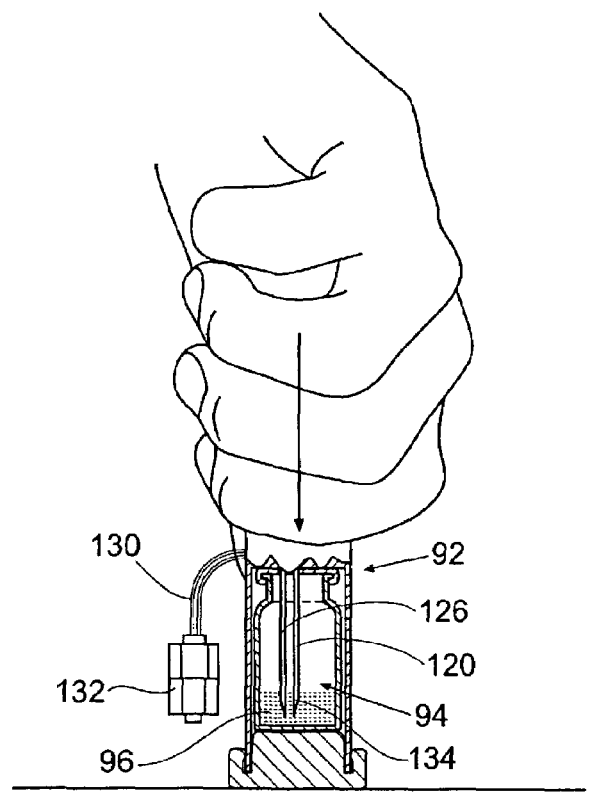

In use (see FIGS. 5 and 6), the physician (or assistant) removes the cap 114 from the applicator 92. As seen in FIG. 5, with the cap 114 removed, the physician slides the first compartment 106 over the vial 94. During this step, the vial 94 can be placed on a counter, table, or other flat support surface. As seen in FIG. 6, the cap 114 is then placed beneath the vial 94 (e.g., on the counter or table), and the physician continues to slide the first compartment 106 over the vial 94, to finish piercing the vial septum 134 with the needles 120 and 126 and locating the vial 94 fully into the first compartment 106. The cap 114 thereafter holds the vial 94 in this position.

As shown in FIG. 7, the cap 119 is then removed from the syringe 98 and residual air is expressed from the syringe 98, e.g., by holding the syringe 98 with the dispensing end 116 upright and gently tapping the syringe 98 until essentially all of the residual air rises to the dispensing end 116 and then advancing the plunger 102 until the air is expelled (not shown).

Figure 8:
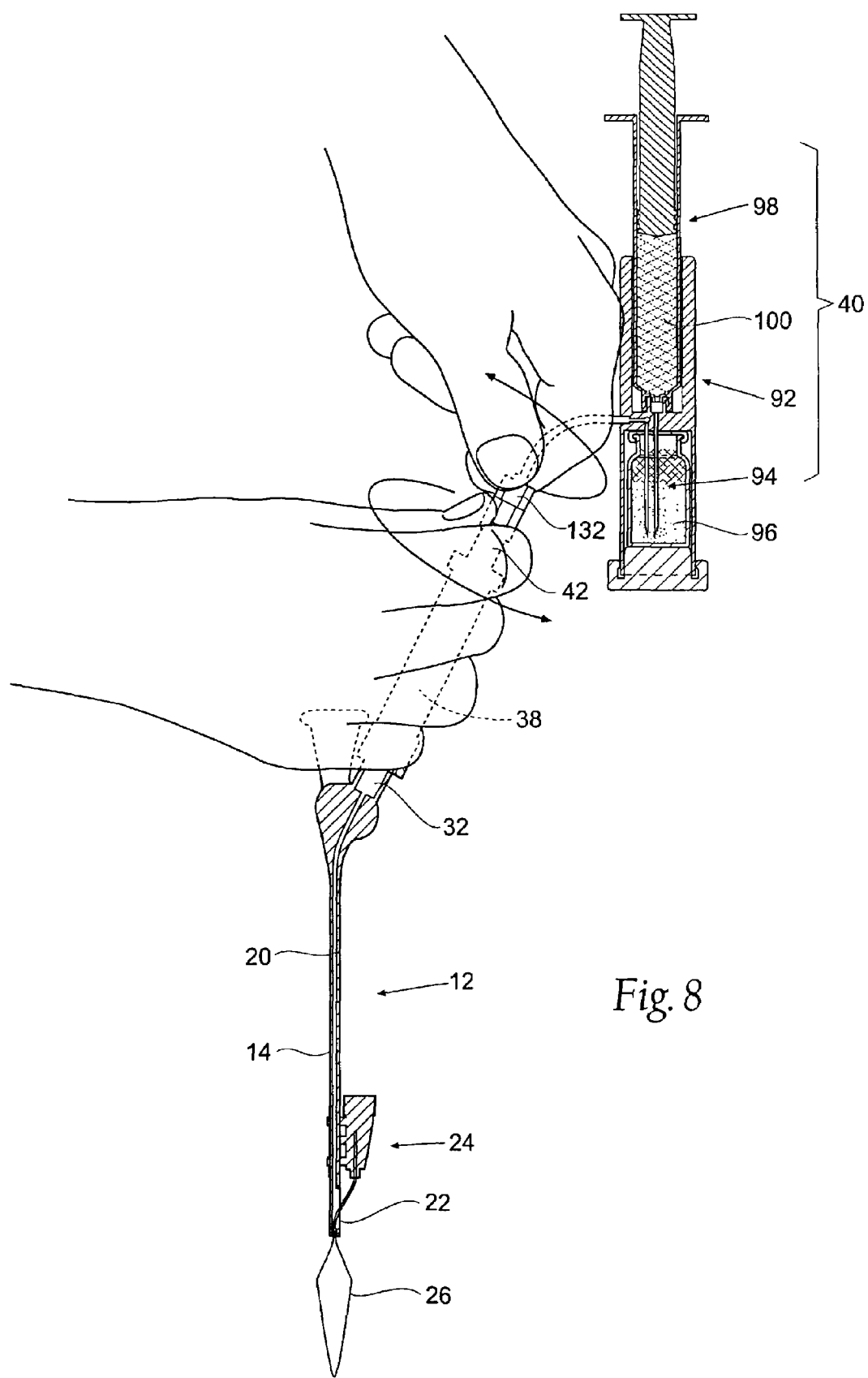

As FIG. 7 shows, the syringe 98 is then placed within the second compartment 108 and rotated (represented by an arrow) to couple the syringe 98 to the first needle 120 through luer fittings 118 and 122. With the syringe 98 and vial 94 in place within the applicator 92 and the formative assembly 40 ready for use, as seen in FIG. 8, the assembly 40 can then be coupled to the mixing assembly 38 (shown in phantom lines) by coupling (represented by arrows) luer fittings 42 and 132.

As will be apparent, alternatively, the syringe 98 can be coupled to the first needle 120 prior to the vial 94 being placed in the first compartment 106.

Figure 9:
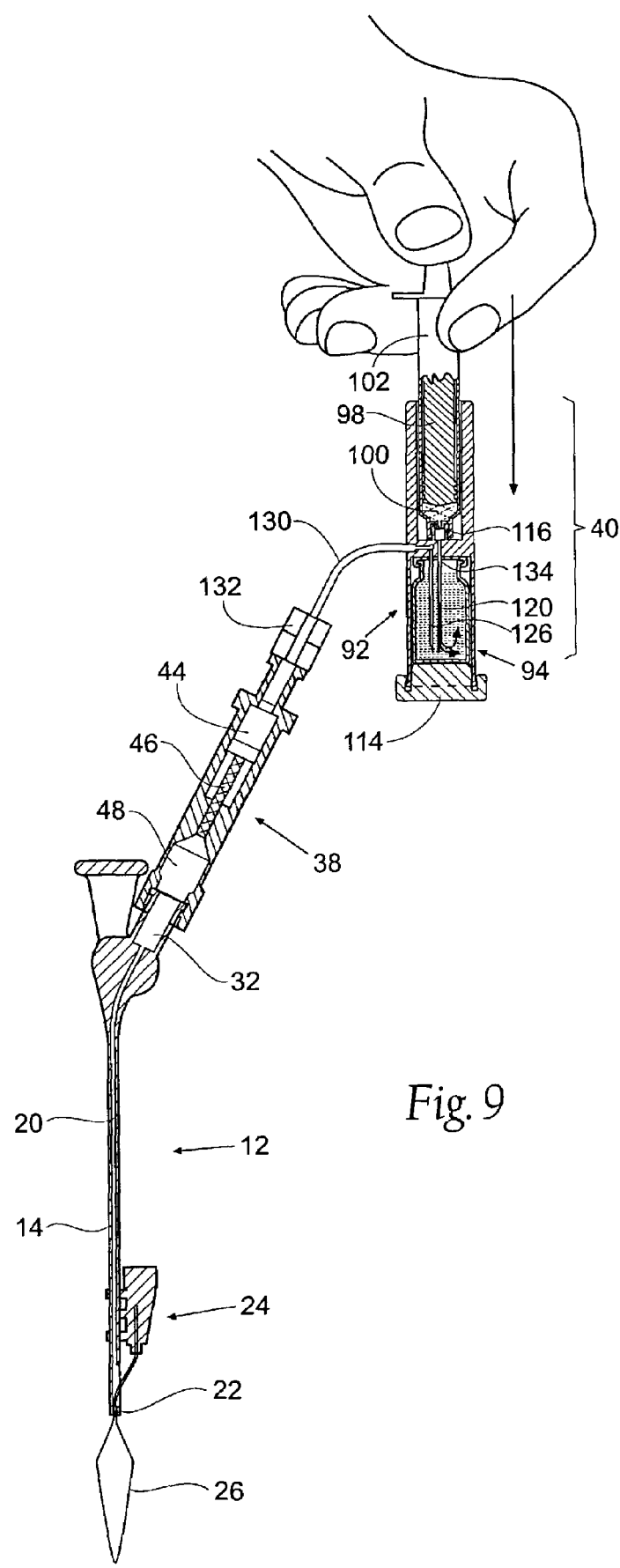

With reference now to FIG. 9, the formative component assembly 40 is then placed in an upright position (i.e., vial septum 134 pointing upward and dispensing end 116 of the syringe 98 pointing downward). The plunger 102 is then advanced (represented by an arrow) to transfer the contents of the syringe 98 through the first needle 120 into the vial 94. If desired, the assembly 18 can be stood on a counter, table, or other flat surface as the plunger 102 is advanced. Alternatively, the plunger 102 can be advanced in conventional fashion by the thumb of the physician while the syringe 98, with attached applicator 92, are held between the forefinger and middle finger, as FIG. 9 shows.

The propulsion of the liquid component 100 into the vial 94 reconstitutes the solid component 96, mixes the components 96 and 100 (represented by arrows in FIG. 9), and begins the reaction process.

Figure 10:
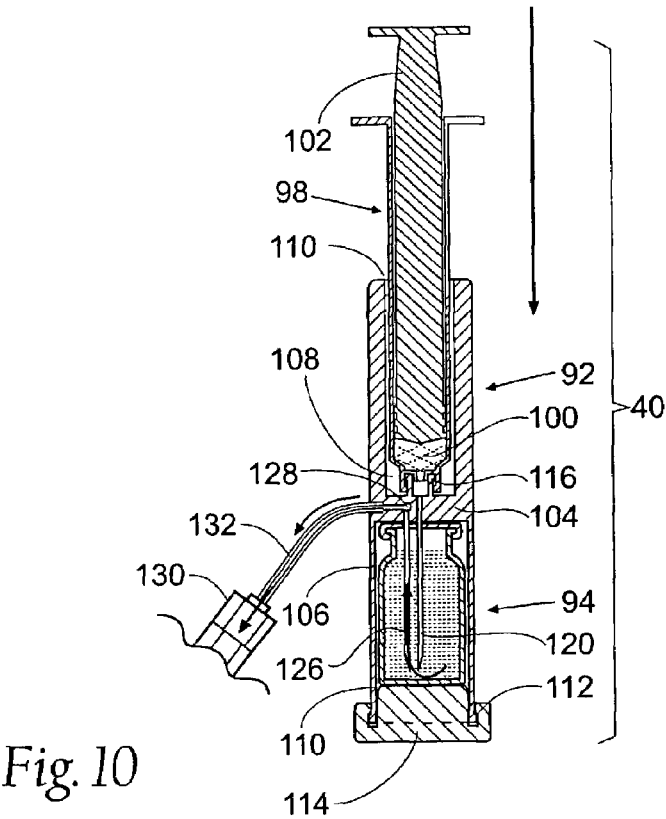

Fluid pressure created by operation of the syringe 98 urges the mixture into and through the second needle 126, into the mixing 38, as indicated by arrows in FIG. 10. The mixing assembly 38 further mixes the mixture and rids the fluid path of residual air, as previously described. The mixture flows through the mixing assembly 38 and through the knot pusher passage 20. The mixture exits the knot pusher 12 through the distal end 16, as FIG. 22 shows.

Figure 11:
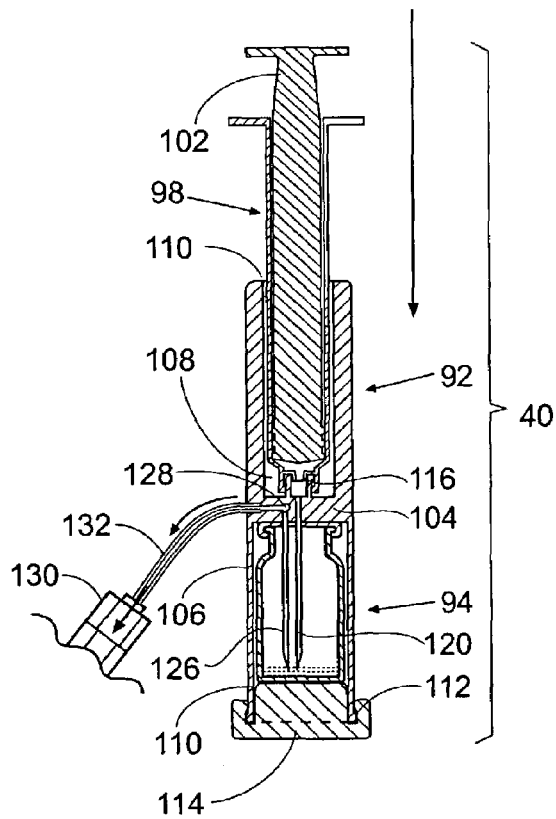
Figure 12:
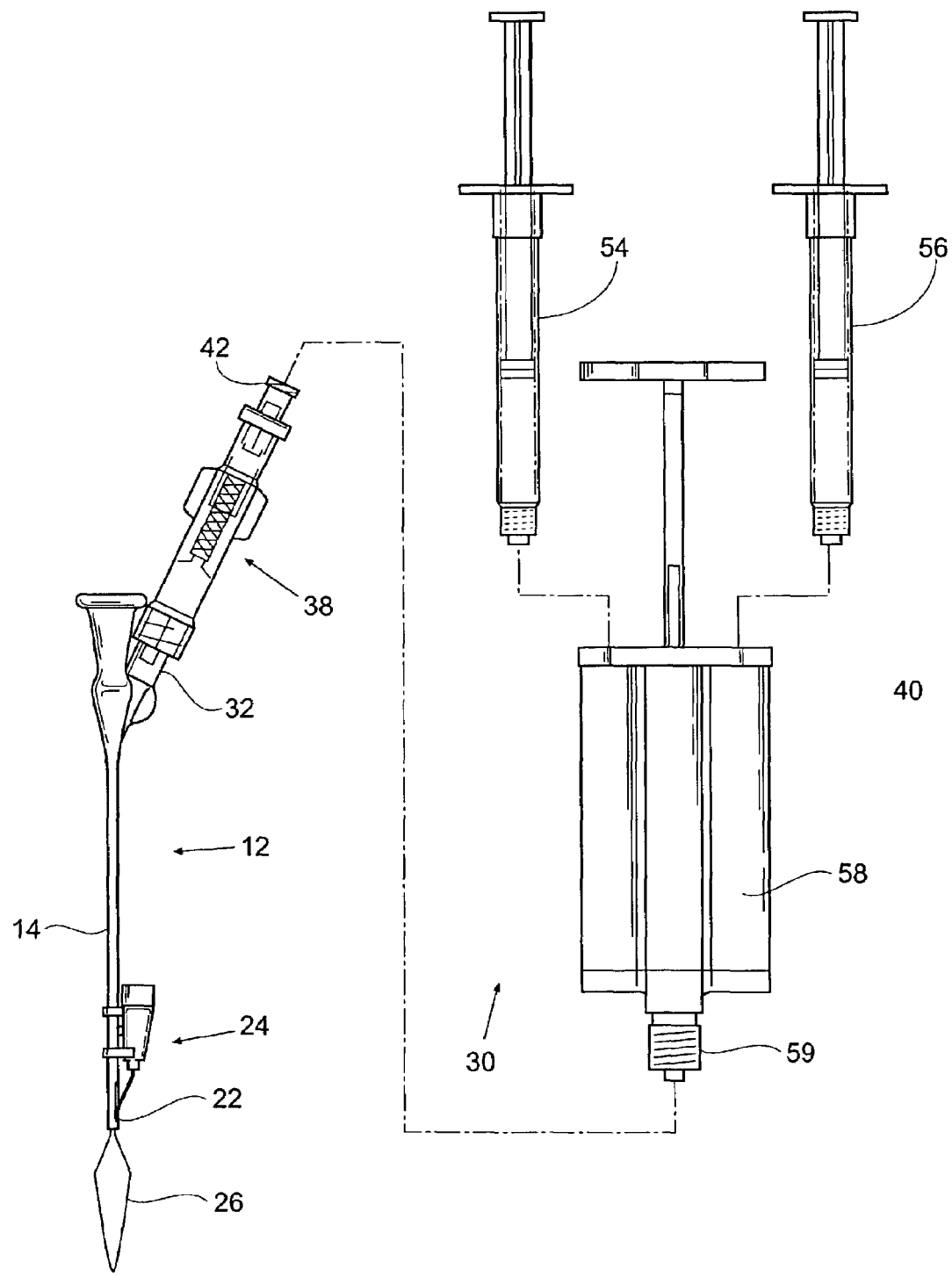
FIG. 12 is a plane view of a system of functional instruments for the closure of incisions and wounds using a suture knot in combination with a biocompatible material composition, the system including a knot pusher as generally shown in FIGS. 2 and 3 and an alternative embodiment of component introducer/mixer assembly comprising two syringes coupled to a holder.
Figure 13:
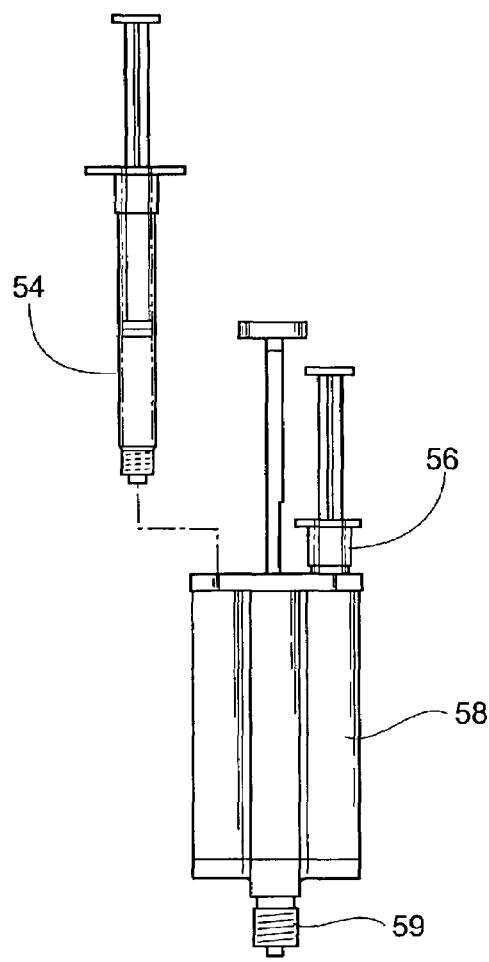
FIG. 13 is a plane exploded view of the component introducer/mixer assembly shown in FIG. 12, with one of the syringes withdrawn from the holder.
Figure 14:
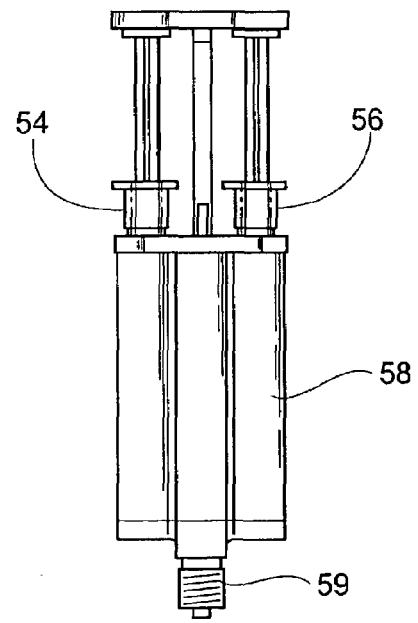
FIG. 14 is an assembled view of the component introducer/mixer assembly shown in FIG. 13.

With reference now to FIG. 11, the plunger 102 is advanced until essentially all of the liquid component 100 is transferred from the syringe 98 to the vial 94. Generally concurrently, the mixture is transferred from the vial 94 into the mixing assembly 38, with only minimal residual mixture remaining in the vial 94. As will apparent to one skilled in the art, the volume of components 96 and 100 are calculated to account for this residual volume.

Further details of the component introducer/mixer assembly 30 just described are disclosed in copending U.S. patent application Ser. No. 10/141,510, filed May 8, 2002 and entitled "Systems, Methods, and Compositions for Achieving Closure of Vascular Puncture Sites," which is incorporated herein by reference.

Figure 15:
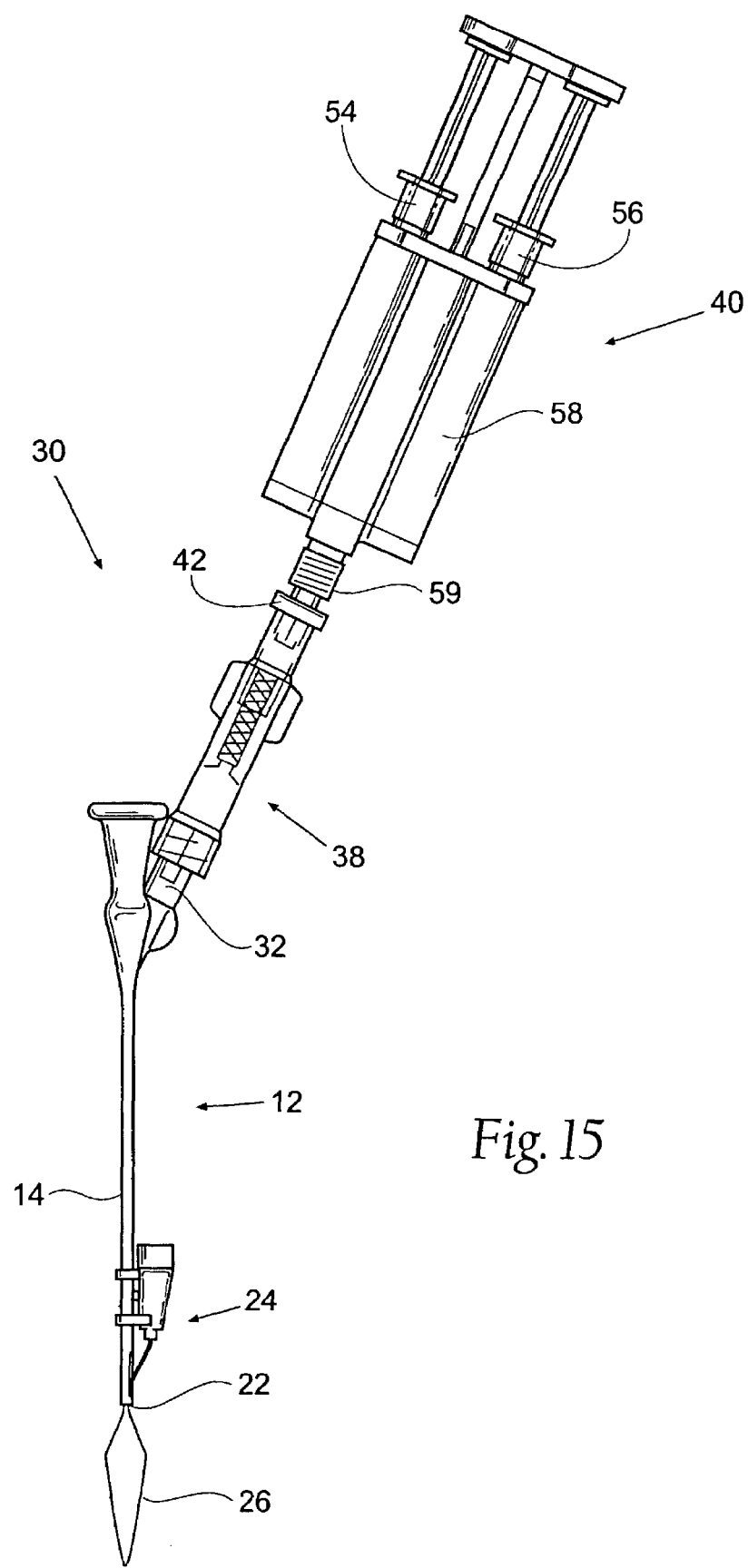
FIG. 15 is a plane view of the component introducer/mixer assembly shown in FIG. 12 coupled for use to the knot pusher shown in FIGS. 2 and 3.

Alternatively (see FIGS. 12 to 15), the formative component assembly 40 can comprise individual syringes 54 and 56 in which the components are separately contained. The syringes 54 and 56 are, in use, coupled to a holder 58. In use, the holder 58 is coupled via a luer fitting 59 to the mixer element 38, as FIG. 15 shows. Further details of this arrangement are disclosed in copending U.S. patent application Ser. No. 09/187,384, filed Nov. 6, 1998 and entitled "Systems and Methods for Applying Cross-Linked Mechanical Barriers," which is incorporated herein by reference.

(iii) The Material Composition

The components 96 and 100 of the material composition can vary. In a preferred embodiment, the solid component 96 comprises an electrophilic (electrode withdrawing) material having a functionality of at least three. The liquid component 100 comprises a solution containing a nucleophilic (electron donator) material and a buffer. When mixed under proper reaction conditions, the electrophilic material and buffered nucleophilic material react, by cross-linking with each other. The cross-linking of the components form the composition. The composition physically forms a mechanical barrier (see FIG. 24), which can also be characterized as a hydrogel.

The type and concentration of a buffer material controls the pH of the liquid and solid components 100 and 96, when brought into contact for mixing. The buffer material desirably establishes an initial pH in numeric terms, as well regulates change of the pH over time.

The Electrophilic Component

In its most preferred form, the electrophilic (electrode withdrawing) material 96 comprises a hydrophilic, biocompatible polymer that is electrophilically derivatized with a functionality of at least three. Examples include poly(ethylene glycol), poly(ethylene oxide), poly(vinyl alcohol), poly(vinylpyrrolidinone), poly(ethyloxazoline), and poly (ethylene glycol)-co-poly(propylene glycol) block copolymers.

As used herein, a polymer meeting the above criteria is one that begins with a multiple arm core (e.g., pentaerythritol) and not a bifunctional starting material, and which is synthesized to a desired molecular weight (by derivatizing the end groups), such that polymers with functional groups greater than or equal to three constitute (according to gel permeation chromatography—GPC) at least 50% or more of the polymer blend.

The material 96 is not restricted to synthetic polymers, as polysaccharides, carbohydrates, and proteins could be electrophilically derivatized with a functionality of at least three. In addition, hybrid proteins with one or more substitutions, deletions, or additions in the primary structure may be used as the material 96. In this arrangement, the protein's primary structure is not restricted to those found in nature, as an amino acid sequence can be synthetically designed to achieve a particular structure and/or function and then incorporated into the material. The protein of the polymer material 96 can be recombinantly produced or collected from naturally occurring sources.

Preferably, the polymer material 96 is comprised of poly(ethylene glycol) (PEG) with a molecular weight preferably between 9,000 and 12,000, and most preferably 10,500±1500. PEG has been demonstrated to be biocompatible and non-toxic in a variety of physiological applications. The preferred concentrations of the polymer are 5% to 35% w/w, more preferably 5% to 20% w/w. The polymer can be dissolved in a variety of solutions, but sterile water is preferred.

The most preferred polymer material 96 can be generally expressed as compounds of the formula:

PEG-(DCR-CG)$_n$

Where:
DCR is a degradation control region.
CG is a cross-linking group.
n≧3

The electrophilic CG is responsible for the cross-linking of the preferred nucleophilic material 96, as well as binding the composition 136 to the like material in the surrounding tissue, as will be described later. The CG can be selected to selectively react with thiols, selectively react with amines, or react with thiols and amines. CG's that are selective to thiols include vinyl sulfone, N-ethyl maleimide, iodoacetamide, and orthopyridyl disulfide. CG's that are selective to amines include aldehydes. Non-selective electrophilic groups include active esters, epoxides, oxycarbonylimidazole, nitrophenyl carbonates, tresylate, mesylate, tosylate, and isocyanate. The preferred CG's are active esters, more preferred, an ester of N-hydroxysuccinimide. The active esters are preferred since they react rapidly with nucleophilic groups and have a non-toxic leaving group, e.g., hydroxysuccinimide.

The concentration of the CG in the polymer material 96 can be used to control the rate of gelation. However, changes in this concentration typically also result in changes in the desired mechanical properties of the hydrogel.

The rate of degradation is controlled by the degradation control region (DCR), the concentration of the CG's in the polymer solution, and the concentration of the nucleophilic groups in the protein solution. Changes in these concentrations also typically result in changes in the mechanical properties of the hydrogel, as well as the rate of degradation.

The rate of degradation (which desirably occurs in about 30 days) is best controlled by the selection of the chemical moiety in the degradation control region, DCR. If degradation is not desired, a DCR can be selected to prevent biodegradation or the material can be created without a DCR. However, if degradation is desired, a hydrolytically or enzymatically degradable DCR can be selected. Examples of hydrolytically degradable moieties include saturated di-acids, unsaturated di-acids, poly(glycolic acid), poly(DL-lactic acid), poly(L-lactic acid),poly(ξ-caprolactone), poly(δ-valerolactone),poly(γ-butyrolactone), poly(amino acids), poly(anhydrides), poly(orthoesters), poly(orthocarbonates), and poly(phosphoesters), and derivatives thereof. A preferred hydrolytically degradable DCR is gluturate. Examples of enzymatically degradable DCR's include Leu-Gly-Pro-Ala (collagenase sensitive linkage) and Gly-Pro-Lys (plasmin sensitive linkage). It should also be appreciated that the DCR could contain combinations of degradable groups, e.g. poly(glycolic acid) and di-acid.

While the preferred polymer is a multi-armed structure, a linear polymer with a functionality, or reactive groups per molecule, of at least three can also be used. The utility of a given PEG polymer significantly increases when the functionality is increased to be greater than or equal to three. The observed incremental increase in functionality occurs when the functionality is increased from two to three, and again when the functionality is increased from three to four. Further incremental increases are minimal when the functionality exceeds about four.

A preferred polymer may be purchased from SunBio Company ((PEG-SG)$_4$, having a molecular weight of 10,500±1500)(which will sometimes be called the "SunBio PEG").

The Nucleophilic Component

In a most preferred embodiment, the nucleophilic material 100 includes non-immunogenic, hydrophilic proteins. Examples include serum, serum fractions, and solutions of albumin, gelatin, antibodies, fibrinogen, and serum proteins. In addition, water soluble derivatives of hydrophobic proteins can be used. Examples include solutions of collagen, elastin, chitosan, and hyaluronic acid. In addition, hybrid proteins with one or more substitutions, deletions, or additions in the primary structure may be used.

Furthermore, the primary protein structure need not be restricted to those found in nature. An amino acid sequence can be synthetically designed to achieve a particular structure and/or function and then incorporated into the nucleophilic material 100. The protein can be recombinantly produced or collected from naturally occurring sources.

The preferred protein solution is 25% human serum albumin, USP. Human serum albumin is preferred due to its biocompatibility and its ready availability.

The uses of PEG polymers with functionality of greater than three provides a surprising advantage when albumin is used as the nucleophilic material 100. When cross-linked with higher functionality PEG polymers, the concentration of albumin can be reduced to 25% and below. Past uses of difunctional PEG polymers require concentrations of albumin well above 25%, e.g. 35% to 45%. Use of lower concentrations of albumin result in superior tissue sealing properties with increased elasticity, a further desired result. Additionally, 25% human serum albumin, USP is commercially available from several sources, however higher concentrations of human serum albumin, USP are not commercially available. By using commercially available materials, the dialysis and ultrafiltration of the albumin solution, as disclosed in the prior art, is eliminated, significantly reducing the cost and complexity of the preparation of the albumin solution.

To minimize the liberation of heat during the cross-linking reaction, the concentration of the cross-linking groups of the fundamental polymer component is preferably kept less than 5% of the total mass of the reactive solution, and more preferably about 1% or less. The low concentration of the cross-linking group is also beneficial so that the amount of the leaving group is also minimized. In a typical clinical application, about 50 mg of a non-toxic leaving group is produced during the cross-linking reaction, a further desired result. In a preferred embodiment, the CG comprising an N-hydroxysuccinimide ester has demonstrated ability to participate in the cross-linking reaction with albumin without eliciting adverse immune responses in humans.

The Buffer Component

In the most preferred embodiment, a PEG reactive ester reacts with the amino groups of the albumin and other tissue proteins, with the release of N-hydroxysuccinimide and the formation of a link between the PEG and the protein. When there are multiple reactive ester groups per PEG molecule, and each protein has many reactive groups, a network of links form, binding all the albumin molecules to each other and to adjacent tissue proteins.

This reaction with protein amino groups is not the only reaction that the PEG reactive ester can undergo. It can also react with water (i.e., hydrolyze), thereby losing its ability to react with protein. For this reason, the PEG reactive ester must be stored dry before use and dissolved under conditions where it does not hydrolyze rapidly. The storage container for the PEG material desirably is evacuated by use of a vacuum, and the PEG material is stored therein under an inert gas, such as Argon or Nitrogen. Another method of packaging the PEG material is to lyophilize the PEG material and store it under vacuum, or under an inert gas, such as Argon or Nitrogen, as will be described in greater detail later. Lyophilization provides the benefits of long term storage and product stability, as well as allows rapid dissolution of the PEG material in water.

The conditions that speed up hydrolysis tend to parallel those that speed up the reaction with protein; namely, increased temperature; increased concentration; and increased pH (i.e., increased alkali). In the illustrated embodiment, temperature cannot be easily varied, so varying the concentrations and the pH are the primary methods of control.

It has been discovered, through bench testing, that when cross-linking the SunBio PEG with albumin (Plasbumin), a range of gelation times between an acceptable moderate time (about 30 seconds) to a rapid time (about 2 seconds) can be achieved by establishing a pH range from about 8 (the moderate times) to about 10 (the rapid times). Ascertaining the cross-linking pH range aids in the selection of buffer materials from among phosphate, tris-hydroxymethylaminomethane (Tris), and carbonate, which are all non-toxic, biocompatible buffers.

Further details of the material composition are found in copending U.S. patent application Ser. No. 09/780,014, filed Feb. 9, 2001, and entitled "Systems, Methods, and Compositions for Achieving Closure of Vascular Puncture Sites," which is incorporated herein by reference.

REPRESENTATIVE EMBODIMENT

In a representative embodiment employed with a 7 FR device, the vial 94 contains 600 mg±10% of lyophilized SunBio PEG-SG (4-arm polyethylene glycol tetrasuccinimidyl glutarate—MW 10,500±1500). Details of the lyophilization process are described in U.S. patent application Ser. No. 10/141,510, filed May 8, 2002 and entitled "Systems, Methods, and Compositions for Achieving Closure of Vascular Puncture Sites," which is incorporated herein by reference. The syringe 98 contains 6 ml of water and 2 ml of buffered 25% w/w human serum albumin, USP. The buffered 25% albumin is made by adding 0.217 g. of Tris-hydroxymethlaminomethane ($C_4H_{11}NO_3$) (FW 121.1) (TRIS Buffer) to 20 cc of Bayer Plasbumin® −25 to obtain a pH between 8.0 and 8.7, most preferably between 8.3 and 8.5.

II. Representative Use of the System

Use of the knot pusher 12 in conventional fashion will form the suture closure 28, as FIGS. 16 to 21 show. As FIG. 22 shows, once coupled to the knot pusher 12, operation of the formative component assembly 40, as previously described, expresses the components 96 and 100, while in liquid form, through the mixer element 38 and through the knot pusher 12. The gelating components 50 flow out the distal end 16 and slot 22 of the knot pusher and into the subcutaneous tissue surrounding the suture closure 28.

The knot pusher 12 is desirably sized to seal the tissue track 34, to block substantial flow in a path up the tissue track 34. Thus, the gelating components 50 are first delivered in a liquid state adjacent to the suture closure 28. The incoming flow, directed in this manner, creates a tissue space about the suture closure 28. The gelating components 50 fill this space. Desirably (see FIG. 23), after first introducing the gelating components 50 at the site of the suture closure 28, the physician slowly withdraws the knot pusher 12 up the tissue tract 34 while still delivering the components 50, to substantially fill the entire tissue tract 34 with the gelating components 50.

In the gelation process, the electrophilic component and the nucleophilic component cross-link, and the developing composition 50 gains cohesive strength to close the suture closure 28 and the tissue tract 34. The electrophilic component also begins to cross-link with nucleophilic groups on the surrounding tissue mass.

Adhesive strength forms, which begins to adhere the developing composition to the surrounding tissue mass.

During the introduction stage, before internal cohesive and tissue adhesive strengths fully develop, a portion of the gelating components 50 can seep through the suture closure 28 and enter the blood vessel. Upon entering the blood stream, the gelating components 50 will immediately experience physical dilution. The dilution expands the distance between the electrophilic component and the nucleophilic component, making crosslinking difficult. In addition, the diluted components now experience an environment having a pH (7.3 to 7.4) lower than the an effective reactive pH for cross-linking (which is above 8) (as an example, a typical gelation time at pH 8.3 is about 15 to 20 seconds, whereas a typical gelation time at pH 7.4 is over 10 minutes). As a result, incidence of cross-linking within the blood vessel, to form the hydrogel composition, is only a fraction of what it is outside the vessel, where gelation continues.

Furthermore, the diluted electrophilic component will absorb nucleophilic proteins present in the blood. This reaction further reduces the reactivity of the electrophilic component. In blood, the diluted electrophilic component is transformed into a biocompatible, non-reactive entity, which can be readily cleared by the kidneys and excreted. The diluted nucleophilic component 100 is a naturally occurring protein that is handled in normal ways by the body.

This stage preferably last about 5 to 30 seconds from the time the physician begins to mix the components 96 and 100.

A second stage begins after the physician has delivered the entire prescribed volume of components 96 and 100 to the tissue mass of the suture closure 28 and tissue tract 34. At this point, the cross-linking of the components 96 and 100 has progressed to the point where a semi-solid gel occupies the formed tissue space. The physician can now applies localized and temporary compression to the exterior skin surface surrounding the tissue track 34.

The application of localized pressure serves two purposes. It is not to prevent blood flow through the tissue track 34, as cross-linking of the components 96 and 100 has already proceeded to create a semi-solid gel having sufficient cohesive and adhesive strength to impede blood flow from the puncture site. Rather, the localized pressure serves to compress the tissue mass about the semi-solid gel mass. This compression brings the semi-solid gel mass into intimate contact with surrounding tissue mass, while the final stages of cross-linking and gelation take place.

Under localized compression pressure, any remnant track of the knot pusher 12 existing through the gel mass will also be closed.

Under localized compression pressure, surface contact between the adhesive gel mass and tissue is also increased, to promote the cross-linking reaction with nucleophilic groups in the surrounding tissue mass. Adhesive strength between the gel mass and tissue is thereby allowed to fully develop, to firmly adhere the gel mass to the surrounding tissue as the solid composition 50 forms in situ.

During this stage, blood will also contact the vessel-side, exposed portion of the gel mass, which now covers the tissue puncture site. The electrophilic component will absorb nucleophilic proteins present in the blood, forming a biocompatible surface on the inside of the vessel.

The second stage preferably last about 3 to 10 minutes from the time the physician withdraws the knot pusher 12. At the end of the second stage, the solid composition 50 has formed (as FIG. 24 shows). Hemostasis has been achieved. The suture ends S1 and S2 can be trimmed at the skin surface, and the individual is free to ambulate and quickly return to normal day-to-day functions.

The mechanical properties of the solid composition 50 are such to form a mechanical barrier. The composition 50 is well tolerated by the body, without invoking a severe foreign body response. Over a controlled period, the material composition 50 is degraded by physiological mechanisms. As the material is degraded, the tissue returns to a quiescent state. The molecules of the degraded genus hydrogel composition are cleared from the bloodstream by the kidneys and eliminated from the body in the urine. In a preferred embodiment of the invention, the material loses its physical strength during the first fifteen days, and totally resorbs in about four to eight weeks, depending upon the person's body mass.

III. Alternative Embodiment

Figure 25:
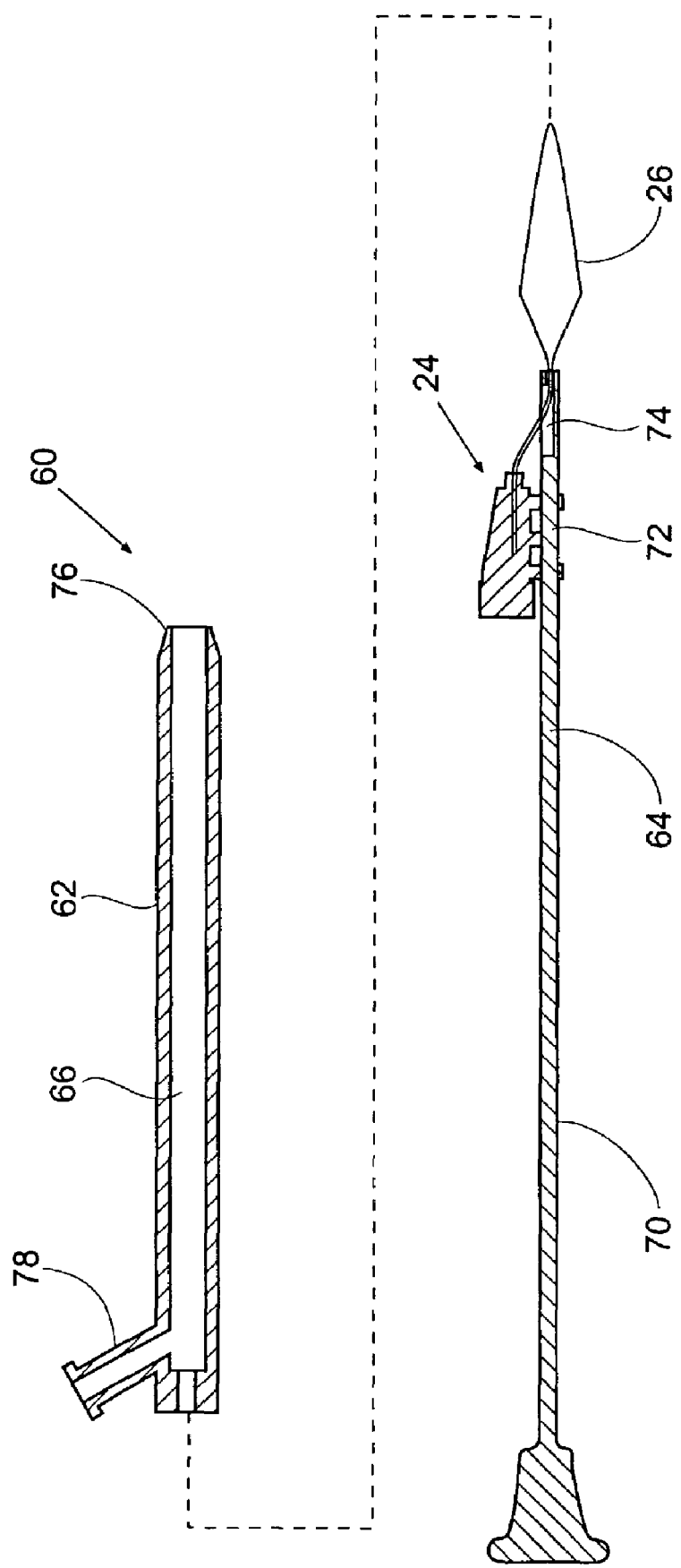
FIG. 25 is a side view, with portions broken away and in section showing an alternative embodiment of a knot pusher usable in association with the system shown in FIG. 1, the knot pusher including an outer sheath and a knot pushing element capable of being inserted coaxially through the outer sheath.
Figure 29:
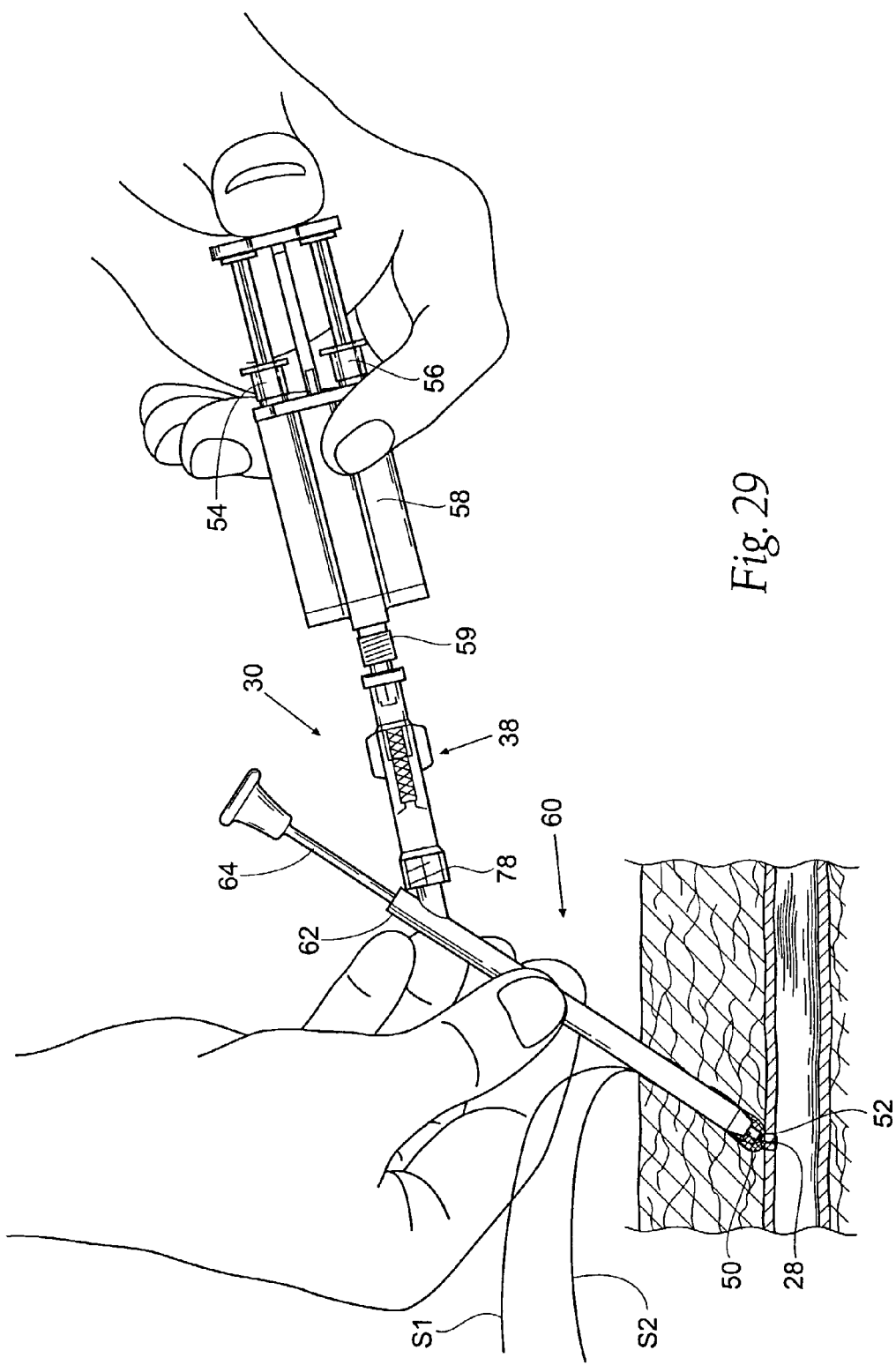

FIG. 25 shows an alternative embodiment of a knot pusher 60 for the closure of incisions and wounds using a suture knot in combination with a biocompatible material composition. Like the knot pusher 12, the knot pusher 60 is well suited for use, for example, at a vascular puncture site following a vascular access procedure. In use (see FIGS. 29 and 30), like the knot pusher 12, the knot pusher 60 accommodates coupling to a component introducer/mixer assembly 30 of the type shown in either FIG. 1 or FIG. 15, to introduce a biocompatible material composition to the site of a suture closure 28 through a transcutaneous tissue tract 34. In FIGS. 29 and 30, an assembly 30 of the type shown in FIG. 15 is shown for purposes of illustration.

Figure 26:
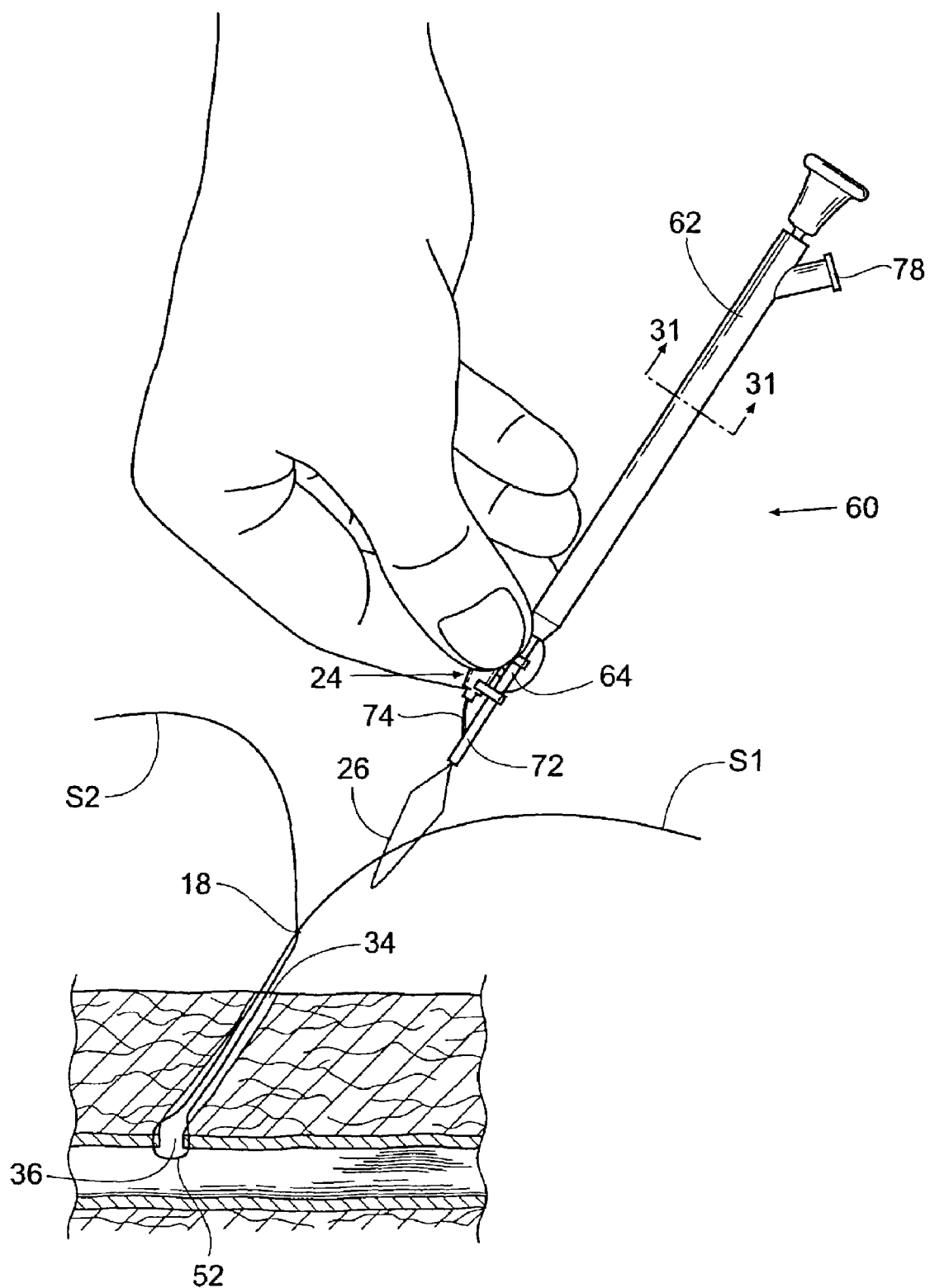
FIG. 26 is a diagrammatic view of blood vessel puncture site formed to enable the delivery of a diagnostic or therapeutic instrument through a vascular sheath, after removal of the diagnostic or thereapeutic instrument and the formation of a slidable knot in a suture loop placed through the puncture site, and as a suture is being threaded in the knot pusher shown in FIG. 25.

In the embodiment shown in FIG. 25, the knot pusher 60 comprises a coaxial assembly of an outer sheath 62 and an inner knot pushing element 64. A lumen 66 in the outer sheath 62 accommodates passage of the knot pushing element 64, as FIG. 26 shows. The lumen 66 includes an open distal end 76 and a port 78 at the proximal end, to which the assembly 30 is coupled during use (as shown in FIG. 29). In this arrangement (see FIG. 31), a passage 68 is formed between the exterior of the knot pushing element 64 and the interior wall of the lumen 66. The port 78 and open distal end 76 communicate with the passage 68. As will be described later, it is through this passage 68 that the material composition 50 is introduced.

Like the knot pusher 12, the knot pusher 60 comprises an elongated body or shaft 70 having a distal end 72. The shaft 14 is sized and configured for passage through the lumen 66 of the outer sheath. It is also sized and configured, when passed through the lumen 66, to have its distal end 72 extend beyond the open distal end 76 of the outer sheath 62, as FIG. 26 shows.

Unlike the knot pusher 12, the knot pusher 60 does not include a through-passage to conduct the biocompatible material composition 50. Instead, in use, the biocompatible material composition is conducted through the passage 68 that is formed between the knot pushing element 64 and the interior wall of the lumen 66.

The knot pusher 60 includes a suture threading fixture 24 of the type previously described in association with the knot pusher 12. The fixture 24 can be releasably carried by the distal end 72 of the shaft 70 in alignment with a slotted passage 74 in the distal end 72 of the shaft 70.

The fixture 24 likewise includes a threader 26 of a type previously described. As before described, the threader 26 desirably comprises a loop of thin, flexible wire that is initially positioned so as to pass through the slotted passage 74 and out the distal end 72 of the shaft 70.

Figure 27:
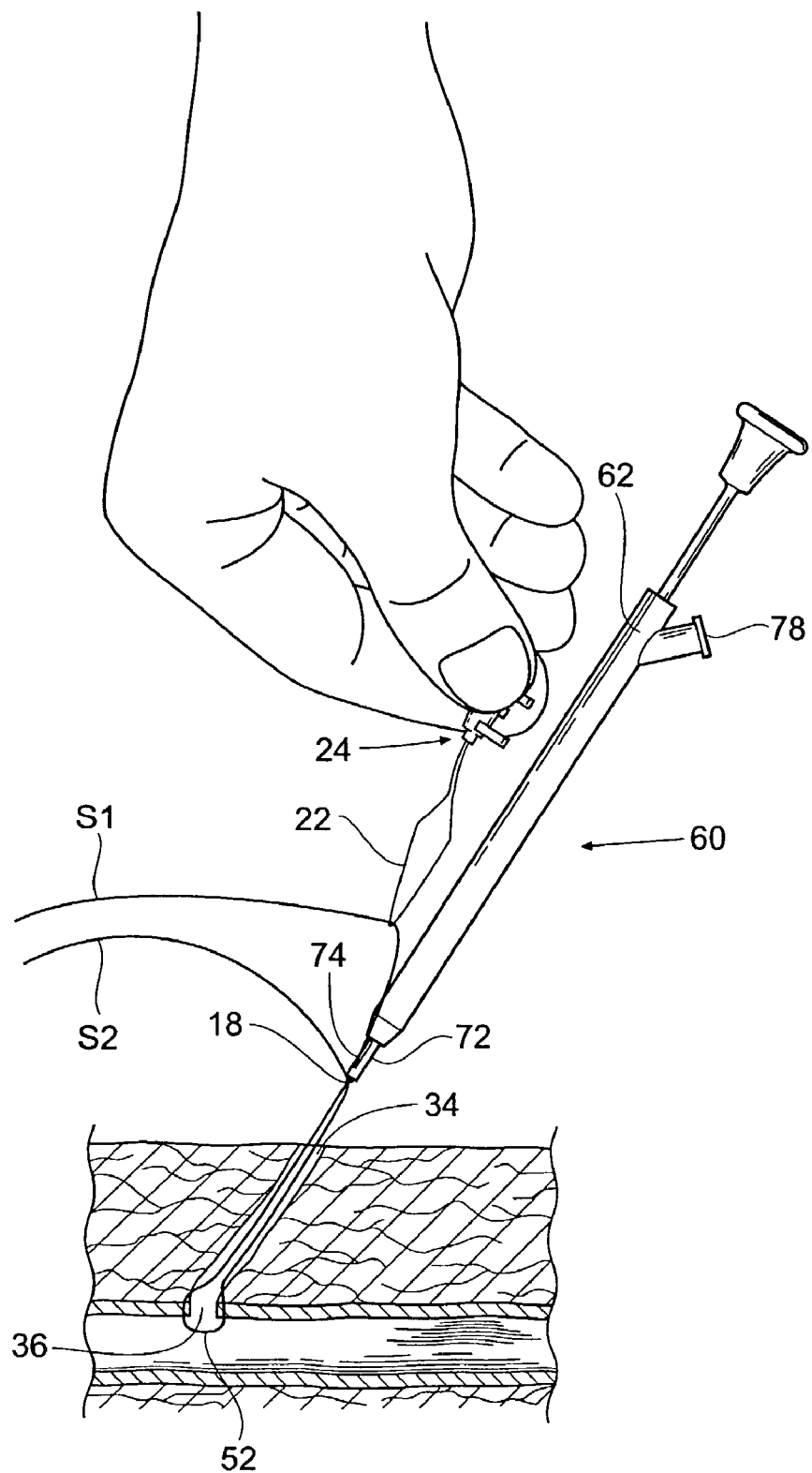
FIG. 27 is a diagrammatic view of the blood vessel puncture site shown in FIG. 26, after threading of suture in the knot pusher and as the knot pusher is advanced toward the tissue tract, pushing the slidable knot.
Figure 28:
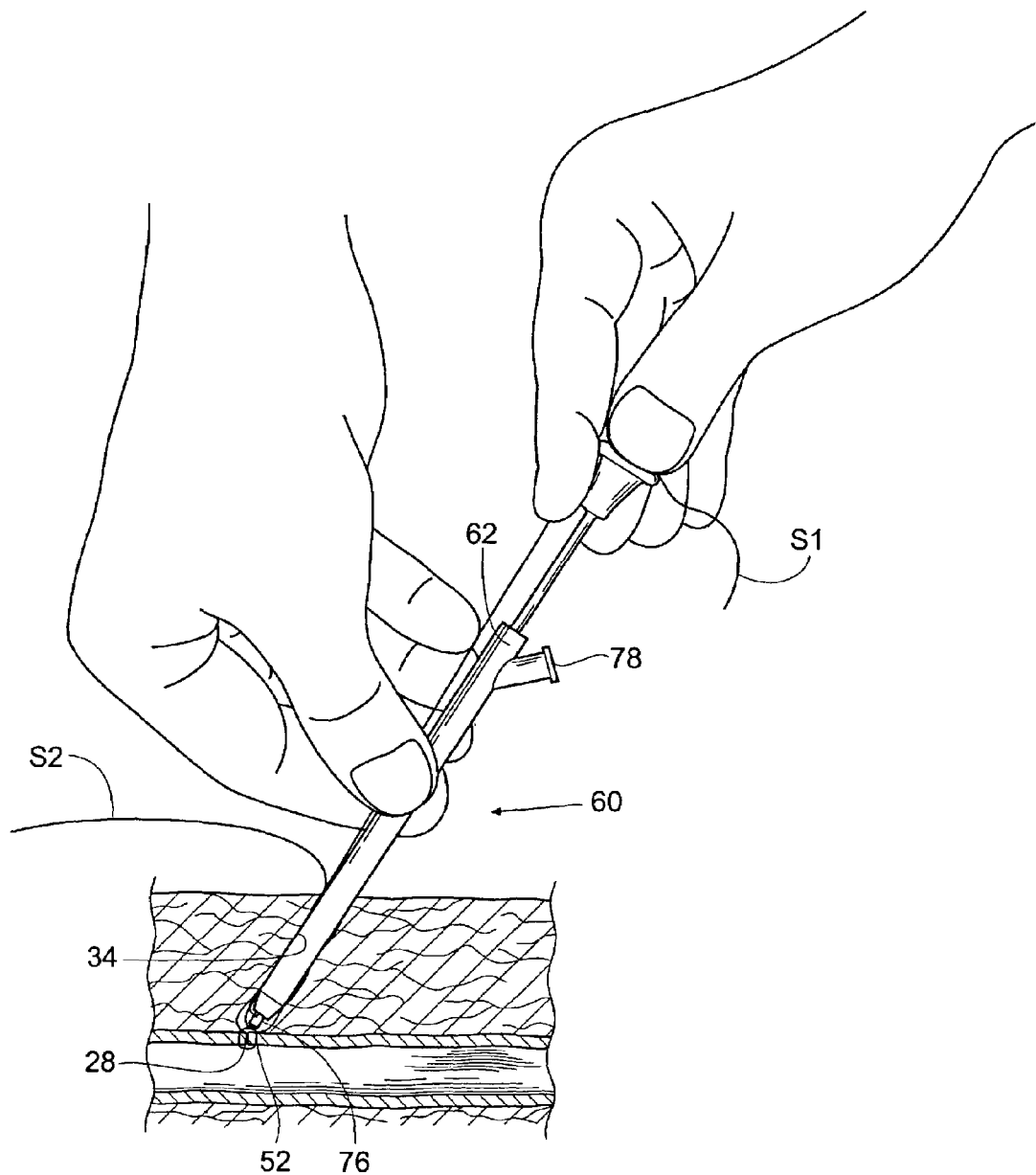
FIG. 28 is a diagrammatic view of the blood vessel puncture site shown in FIG. 27, as the knot pusher is advanced through the tissue tract to form a suture closure at the vessel puncture site.

In use, with the fixture 24 unattached, the knot pushing element 64 is passed through the lumen 66 of outer sheath 62. The threader 26 can then be passed through the slotted passage 74, which is exposed beyond the distal end 76 of the outer sheath 62. If desired, the fixture 24 can also be releasably secured to the distal end 72 of the knot pushing element 64 (as FIG. 26 shows). e After the slidable knot 18 is formed (as previously described), the attending physician captures a free end S1 of the suture within the loop of the threader 26 (as FIG. 27 shows). Freeing the fixture 24 from the distal end 72, the physician pulls the fixture 24 distally to draw the threader 26 and, with it, the free end S1 of the suture through the slotted passage 74. Upon releasing the free end S1 of the suture from the threader 26, and discarding the fixture 24, the physician can then urge the knot pushing element 64 and the outer sheath 62 as an assembled unit through the tissue tract 34 (as FIG. 28 shows). Holding the free suture end S1, the physician advances the assembled knot pusher 60 to tighten the slidable knot 18 within the tissue tract 34, as FIG. 28 shows. The knot pusher 60 engages and advances the slidable knot 18 over the free end S1 of the suture, to close the suture loop 20 and bring the edges of the puncture site 36 into apposition. The slidable knot 18 can then be tightened by pulling on the other free end S2 of the suture, forming a suture closure 28 (shown in FIG. 28). In this arrangement, the suture end S1 serves as a guide wire, to locate and guide the assembled knot pusher 60 generally over the center of the suture closure 28.

Upon forming the suture closure 28 using the knot pusher 60 in the manner just described, the component introducer/mixer assembly 30 can be assembled and coupled to the port 78 of the outer sheath 62(see FIG. 29). The assembly 30 is manipulated in the manner previously described to introduce a biocompatible material composition 50 through the passage 68 and out the open distal end 76 of the outer sheath 62. The composition 50 is placed about the suture closure 28 outside the blood vessel. Desirably (see FIG. 30), by simultaneously withdrawing the knot pusher 60 up the tissue tract 34 as the composition 50 is conducted out the open distal end 76, the composition 50 can also be placed in at least portion of the tissue tract 34. Most desirably (as FIG. 30 shows), at the end of the procedure, the composition 50 fills the tissue tract 34.

As already described, the biocompatible material composition 50 desirably produces a solid, three dimensional matrix that prevents seepage of blood and fluids through the suture closure 28 and up the tissue tract 34. The knot pusher 60 thereby creates a dry closure, which is substantially free of blood or fluid leakage about the suture closure 28 and in the tissue tract 34.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A method for sealing a suture knot comprising the steps of
    placing a suture loop through tissue to join tissue,
    tying the suture loop to form a suture knot, and
    discharging a liquid closure material comprising an electrophilic component comprising a hydrophilic, biocompatible polymer that is electrophilically derivatized with a functionality of at least three and a solution containing a nucleophilic component comprising recombinant or natural serum albumin in a concentration of 25% or less and a buffer component adjacent the suture knot, the liquid closure material cross-linking after discharge to form a solid closure adjacent the suture knot having cohesive and tissue adhesive strength to impede blood flow without clot formation.

2. A method according to claim 1 wherein the forming step includes manipulating a knot pusher.

3. A method according to claim 2 wherein the discharging step includes discharging the liquid closure material through the knot pusher.

4. A method according to claim 1 wherein the polymer comprises poly(ethylene glycol) (PEG).

5. A method according to claim 4 wherein the recombinant or natural serum albumin comprises human serum albumin.

6. A method for sealing a puncture site in a blood vessel comprising the steps of
    placing a suture loop through tissue on opposite sides of the puncture site,
    tying the suture loop to form a suture knot at the puncture site, and
    discharging a liquid closure material comprising an electrophilic component comprising a hydrophilic, biocompatible polymer that is electrophilically derivatized with a functionality of at least three and a solution containing a nucleophilic component comprising recombinant or natural serum albumin in a concentration of 25% or less and a buffer component adjacent the suture knot, the liquid closure material cross-linking after discharge to form a solid closure adjacent the suture knot having cohesive and tissue adhesive strength to impede blood flow without clot formation.

7. A method according to claim 6 wherein the forming step includes manipulating a knot pusher.

8. A method according to claim 7 wherein the discharging step includes discharging the liquid closure material through the knot pusher.

9. A method according to claim 6 wherein the polymer comprises poly(ethylene glycol) (PEG).

10. A method according to claim 9 wherein the recombinant or natural serum albumin comprises human serum albumin.

* * * * *

UNITED STATES PATENT AND TRADEMARK OFFICE
CERTIFICATE OF CORRECTION

PATENT NO. : 7,351,249 B2
APPLICATION NO. : 10/212472
DATED : April 1, 2008
INVENTOR(S) : Olexander Hnojewyj et al.

It is certified that error appears in the above-identified patent and that said Letters Patent is hereby corrected as shown below:

On the Title Page, Item (74) Attorney, Agent, or Firm, delete "Krumholz" and substitute -- Kromholz --.

Signed and Sealed this

Twenty-second Day of July, 2008

JON W. DUDAS
*Director of the United States Patent and Trademark Office*